(12) United States Patent
Brahma et al.

(10) Patent No.: US 12,353,136 B2
(45) Date of Patent: Jul. 8, 2025

(54) FLOW CELL COATING METHODS

(71) Applicant: ILLUMINA, INC., San Diego, CA (US)

(72) Inventors: Neil Brahma, San Diego, CA (US); Tyler J. Dill, San Diego, CA (US); Michelle Kate Fu, San Diego, CA (US); Brian A. Hanos, Carlsbad, CA (US); Sahngki Hong, San Diego, CA (US); Brinda Kodira Cariappa, San Diego, CA (US); Lewis J. Kraft, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 725 days.

(21) Appl. No.: 17/550,681

(22) Filed: Dec. 14, 2021

(65) Prior Publication Data

US 2022/0187710 A1 Jun. 16, 2022

Related U.S. Application Data

(60) Provisional application No. 63/125,716, filed on Dec. 15, 2020.

(51) Int. Cl.
*G03F 7/20* (2006.01)
*G01N 21/64* (2006.01)
(Continued)

(52) U.S. Cl.
CPC ....... *G03F 7/2022* (2013.01); *G01N 21/6428* (2013.01); *G01N 21/6456* (2013.01);
(Continued)

(58) Field of Classification Search
None
See application file for complete search history.

(56) References Cited

U.S. PATENT DOCUMENTS

| 8,101,244 B2 | 1/2012 | Clarke et al. |
| 9,707,584 B2 | 7/2017 | Giusti et al. |
| (Continued) | | |

FOREIGN PATENT DOCUMENTS

| CN | 106948014 B | 3/2019 |
| EP | 1477230 A1 | 11/2004 |
| (Continued) | | |

*Primary Examiner* — Alexander M Weddle
(74) *Attorney, Agent, or Firm* — Dierker & Kavanaugh P.C.

(57) ABSTRACT

In an example method, a water-soluble protective coating solution is applied over a bonding region and either i) a patterned region of a patterned structure or ii) a lane region of a non-patterned structure. The patterned region includes depressions having at least a polymeric hydrogel therein, and interstitial regions separating the depressions. The lane region includes a lane having at least the polymeric hydrogel therein. The water-soluble protective coating solution is dried to form a solid coating or a gel coating over the bonding region and over either i) the patterned region or ii) the lane region. Portions of the solid coating or the gel coating are selectively removed from the bonding region while leaving other portions of the solid coating or the gel coating over either i) the patterned region or ii) the lane region.

8 Claims, 13 Drawing Sheets

(51) Int. Cl.
  *G03F 7/16* (2006.01)
  *C12Q 1/6874* (2018.01)
  *G03F 7/038* (2006.01)

(52) U.S. Cl.
  CPC ........... *G03F 7/168* (2013.01); *C12Q 1/6874* (2013.01); *G01N 2021/6439* (2013.01); *G03F 7/038* (2013.01)

(56) References Cited

U.S. PATENT DOCUMENTS

| | | | |
|---|---|---|---|
| 2012/0316086 A1* | 12/2012 | Lin | G01N 27/447 |
| | | | 506/26 |
| 2016/0288414 A1 | 10/2016 | Ozbolat et al. | |
| 2018/0327832 A1* | 11/2018 | Ramirez | B01L 3/502707 |
| 2020/0047401 A1 | 2/2020 | Yu et al. | |
| 2020/0238276 A1* | 7/2020 | Khurana | C12N 15/1065 |
| 2022/0100091 A1 | 3/2022 | Hong et al. | |

FOREIGN PATENT DOCUMENTS

| | | | | |
|---|---|---|---|---|
| WO | 2011139344 A2 | 11/2011 | | |
| WO | 2019241103 A1 | 12/2019 | | |
| WO | WO-2020005503 A1 * | 1/2020 | ......... | B01J 19/0046 |
| WO | 2020131354 A1 | 6/2020 | | |
| WO | 2020167622 A1 | 8/2020 | | |

* cited by examiner

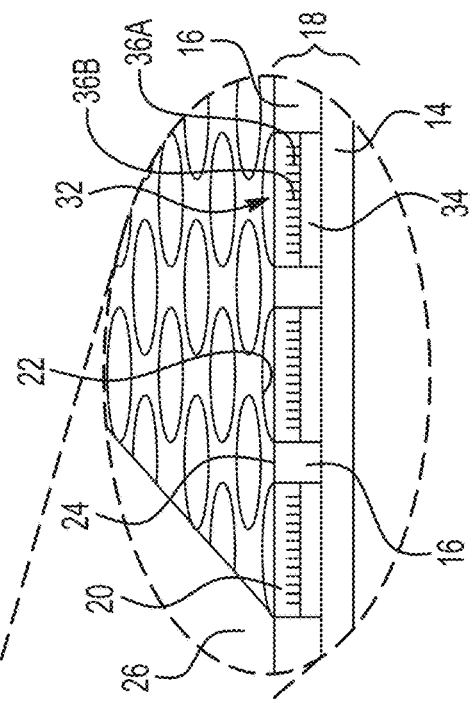
FIG. 1B
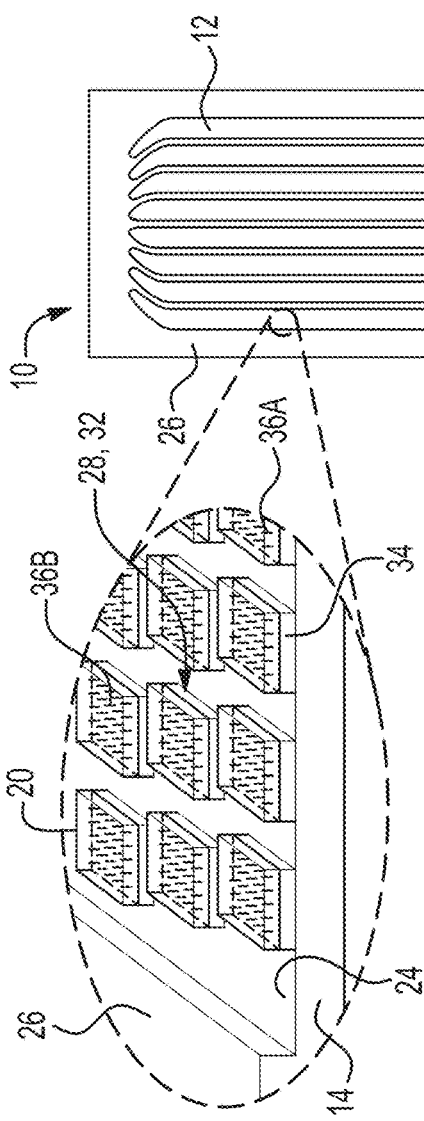
FIG. 1A
FIG. 1C
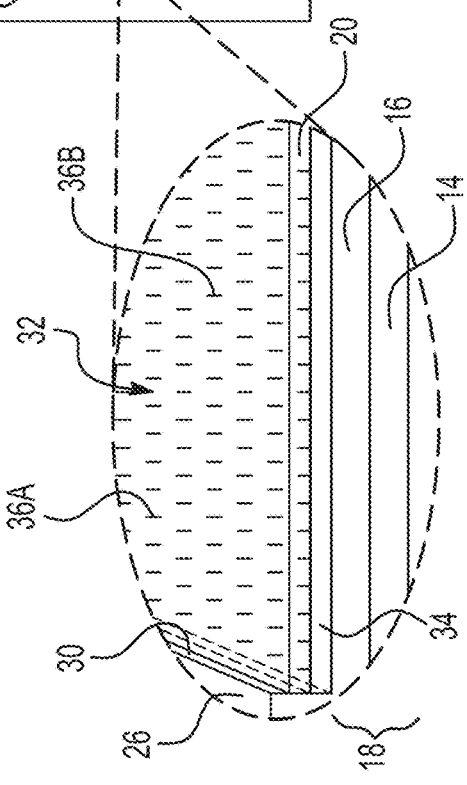
FIG. 1D

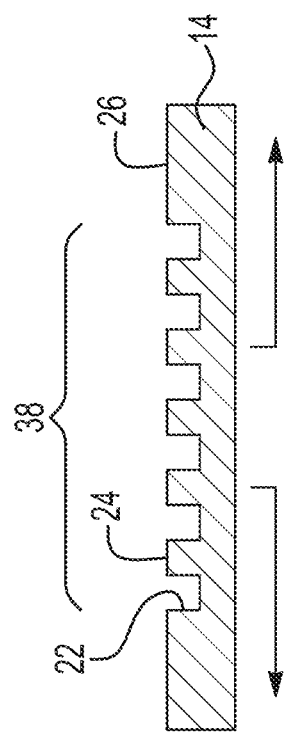
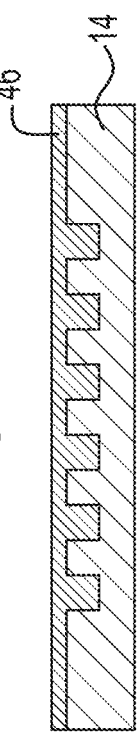
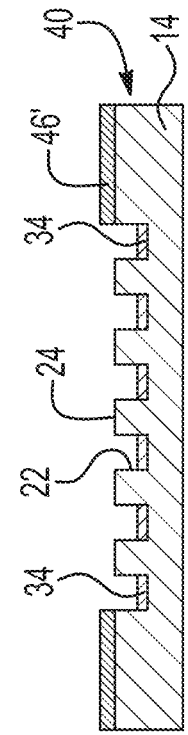
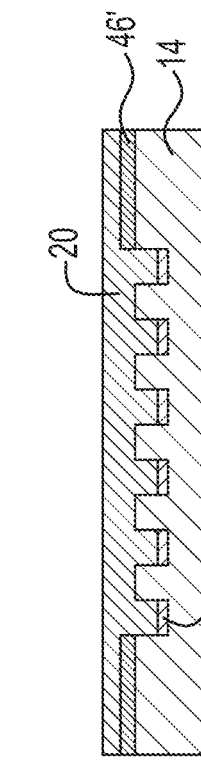
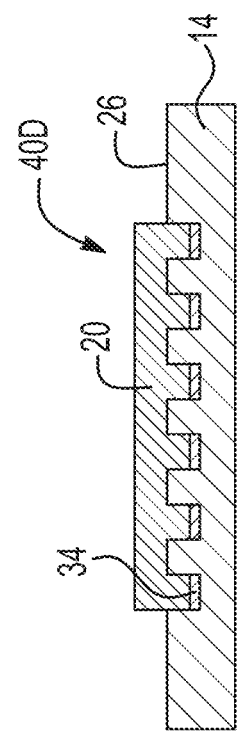
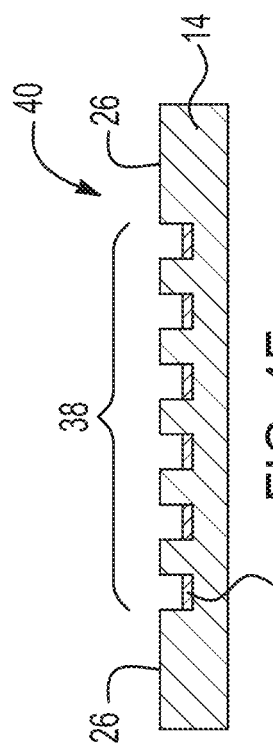
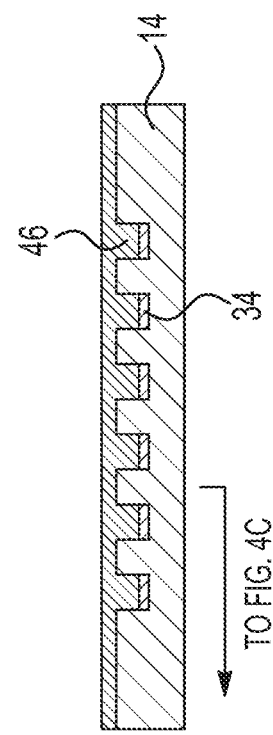

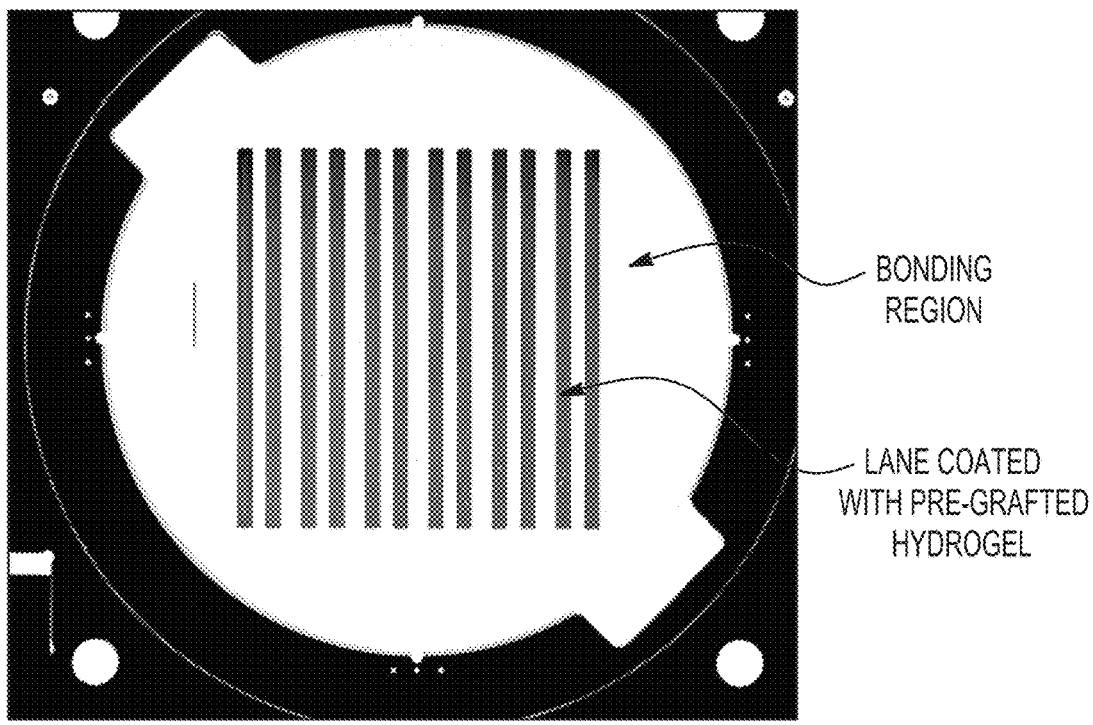
FIG. 12
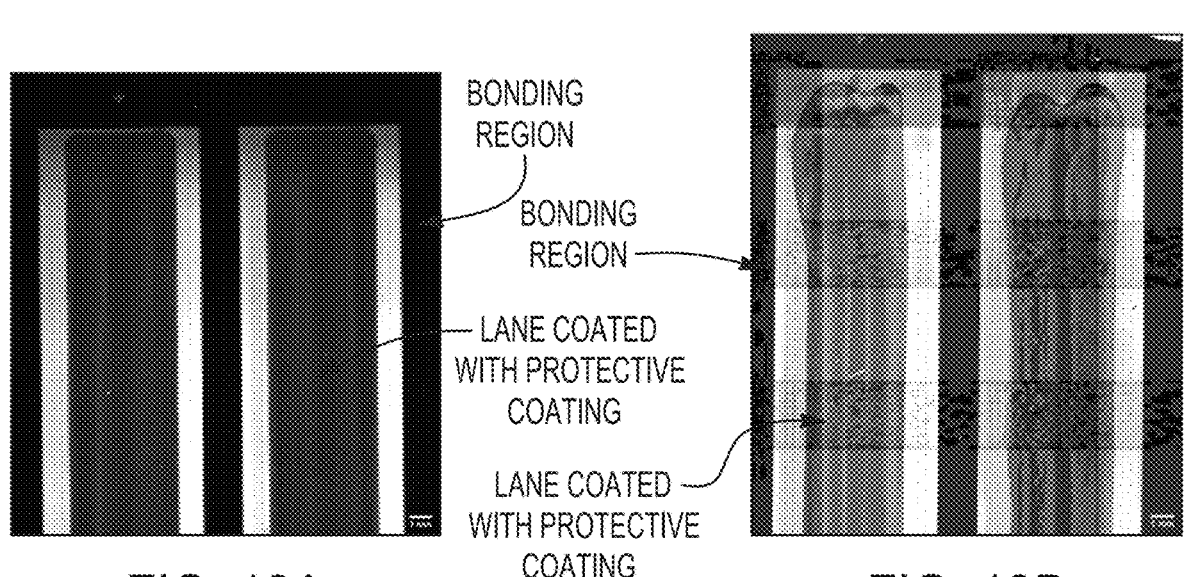
FIG. 13A
FIG. 13B

FLOW CELL COATING METHODS

CROSS-REFERENCE TO RELATED APPLICATIONS

This application claims the benefit of U.S. Provisional Application Ser. No. 63/125,716, filed Dec. 15, 2020, the contents of which is incorporated by reference herein in its entirety.

BACKGROUND

Polymer-coated substrates are used in many technological applications. In an example, implantable medical devices can be coated with biologically inert polymers. In another example, a flow cell includes a polymer-coated surface, which is used in the preparation and/or analysis of biological molecules. Molecular analyses, such as certain nucleic acid sequencing methods, rely on the attachment of nucleic acid strands to the polymer-coated surface. Protective coatings have also been applied on polymer-coated surfaces in order to protect the surfaces, e.g., until they are used in nucleic acid sequencing methods. Some techniques for depositing the protective coating on the polymer-coated surfaces can contaminate other regions of the flow cell, such as bonding regions.

SUMMARY

Disclosed herein are methods that deposit protective coatings or other active area material with high precision. Some examples of the method disclosed herein enable the simultaneous preparation of i) the protective coating over the active areas of the substrate using blanket deposition techniques, such as spin coating or dunk coating, and ii) the bonding region, which is free of the protective coating. During these methods, the active areas may be continuously hydrated or coated, which protects the surface chemistry from degradation, such as from processing conditions.

A first example of these methods comprises applying a water-soluble protective coating solution over a bonding region and over either i) a patterned region of a patterned structure, the patterned region including depressions having at least a polymeric hydrogel therein, and interstitial regions separating the depressions or ii) a lane region of a non-patterned structure, the lane region including a lane having at least the polymeric hydrogel therein; drying the water-soluble protective coating solution to form a solid coating or a gel coating over the bonding region and over either i) the patterned region or ii) the lane region; and selectively removing portions of the solid coating or the gel coating from the bonding region while leaving other portions of the solid coating or the gel coating over either i) the patterned region or ii) the lane region.

In one instance, prior to applying the water-soluble protective coating solution, the first example method may further comprise applying a photoresist over the bonding region and over either i) the patterned region or ii) the lane region; and patterning the photoresist to generate an insoluble photoresist on the bonding region and to remove the photoresist from either i) the patterned region or ii) the lane region. In one example, the water-soluble protective coating solution is applied over the insoluble photoresist, and selectively removing the portions of the solid coating or the gel coating from the bonding region involves lifting off the insoluble photoresist in a remover, wherein the solid coating or the gel coating is insoluble in the remover. In this instance, the photoresist is applied and patterned prior to the polymeric hydrogel being introduced into the depressions or into the lane, and after the photoresist is applied and patterned, but before the water-soluble protective coating solution is applied, the first example method further comprises depositing the polymeric hydrogel over either i) the insoluble photoresist, the depressions, and the interstitial regions or ii) the insoluble photoresist and the lane; and polishing the polymeric hydrogel from at least the insoluble photoresist.

In another instance, after drying the water-soluble protective coating solution, the first example method further comprises applying a photoresist over the solid coating or the gel coating; and patterning the photoresist to remove the photoresist from the portions of the solid coating or the gel coating over the bonding region and to generate an insoluble photoresist over the other portions of the solid coating or the gel coating over either i) the patterned region or ii) the lane region. In this instance, selectively removing the portions of the solid coating or the gel coating from the bonding region involves exposing the portions to a dry etch or a water rinse while the insoluble photoresist is in place. In this instance, the first example method further comprises lifting off the insoluble photoresist in a remover, wherein the solid coating or the gel coating is insoluble in the remover.

In still another instance, the patterned structure or the non-patterned structure is a multi-layer stack including a transparent base support, a patterned mask layer over the transparent base support, and a patterned transparent layer over the patterned mask layer and the transparent base support; a pattern of the patterned mask layer corresponds with the bonding region; and after drying the water-soluble protective coating solution, the first example method further comprises applying a negative photoresist over the solid coating or the gel coating, and exposing the negative photoresist to light through the transparent base support, whereby portions of the negative photoresist overlying either i) the patterned region or ii) the lane region define the insoluble photoresist, and portions of the negative photoresist overlying the patterned mask layer and the bonding region become soluble. In this instance, selectively removing the portions of the solid coating or the gel coating from the bonding region involves exposing the portions to a developer of the negative photoresist. In this instance, the first example method further comprises lifting off the insoluble photoresist in a solvent to which the solid coating or the gel coating is inert.

In yet another instance, after drying the water-soluble protective coating solution, the first example method further comprises selectively applying a metal layer over the other portions of the solid coating or the gel coating; selectively removing the portions of the solid coating or the gel coating from the bonding region involves exposing the portions to a dry etch while the metal layer is in place; and after selectively removing the portions of the solid coating or the gel coating, the method further comprising removing the metal layer.

In other instances, selectively removing the portions of the solid coating or the gel coating from the bonding region involves i) laser patterning the portions of the solid coating or the gel coating over the bonding region, or ii) timed dry etching the solid coating or the gel coating until the bonding region is exposed.

In a further instance, the first example method utilizes the patterned structure, and wherein prior to applying the water-soluble protective coating solution, the first method further comprises forming the patterned structure by: applying a metal layer over a substrate; applying a photoresist over the metal layer; patterning the photoresist to generate an insoluble photoresist that defines a depression pattern; etching portions of the metal layer and underlying portions of the substrate according to the depression pattern to form the depressions in the substrate; removing the insoluble photoresist; and applying the polymeric hydrogel in the depressions and over remaining portions of the metal layer. In this instance, the water-soluble protective coating solution is applied over the polymeric hydrogel; selectively removing the portions of the solid coating or the gel coating from the bonding region involves lifting off the metal layer in a remover, wherein the solid coating or the gel coating is insoluble in the remover; and the polymeric hydrogel and the solid coating or the gel coating on the metal layer is lifted off with the metal layer.

It is to be understood that any features of the first example method may be combined together in any desirable manner and/or may be combined with any of the examples disclosed herein to achieve the benefits as described in this disclosure, including, for example, the ability to keep the flow cell surface chemistry hydrated throughout the method.

A second example of these methods comprises applying a water-soluble protective coating solution over either i) a patterned region of a patterned structure, the patterned region including depressions having at least a polymeric hydrogel therein and interstitial regions separating the depressions, or ii) a lane region of a non-patterned structure, the lane region including a lane having at least the polymeric hydrogel therein, whereby a hydrophobic bonding region of the patterned structure remains exposed; and drying the water-soluble protective coating solution to form a solid coating or a gel coating over either i) the patterned region or ii) the lane region.

It is to be understood that any features of the second example method may be combined together in any desirable manner. Moreover, it is to be understood that any combination of features of the first example method and/or of the second example method may be used together, and/or may be combined with any of the examples disclosed herein to achieve the benefits as described in this disclosure, including, for example, the ability to keep the flow cell surface chemistry hydrated throughout the method.

A third example of these other methods comprises patterning a metal layer on a transparent base support to define i) metal posts separated by first interstitial regions of the transparent base support, and ii) a bonding region of the transparent base support; generating an insoluble negative photoresist over the first interstitial regions and the bonding region; etching the metal posts to expose second interstitial regions of the transparent base support; applying a polymeric hydrogel over the insoluble photoresist and the second interstitial regions; applying a water-soluble protective coating solution over the polymeric hydrogel; drying the water-soluble protective coating solution to form a solid coating or a gel coating over the polymeric hydrogel; and lifting off the insoluble negative photoresist to expose coated functionalized pads, the bonding region, and the first interstitial regions.

In one instance of the third example method, generating the insoluble negative photoresist involves applying a negative photoresist over the metal posts, the first interstitial regions, and the bonding region; exposing the negative photoresist to light through the transparent base support, whereby portions of the negative photoresist overlying the first interstitial regions and the bonding region define the insoluble negative photoresist, and portions of the negative photoresist overlying the metal posts become soluble; and removing the soluble portions of the negative photoresist. In this instance, patterning the metal layer involves: imprinting a resin layer of a multi-layer stack to form a depression pattern and a bonding region pattern, wherein the multi-layer stack includes the resin layer over the metal layer over a base support; and etching the resin layer and the metal layer at the depression pattern and the bonding region pattern until the first interstitial regions of the transparent base support and the bonding region of the transparent base support are exposed.

It is to be understood that any features of the third example method may be combined together in any desirable manner. Moreover, it is to be understood that any combination of features of the first, second, and/or third example methods may be used together, and/or may be combined with any of the examples disclosed herein to achieve the benefits as described in this disclosure, including, for example, the ability to keep the flow cell surface chemistry hydrated throughout the method.

Other examples of the method disclosed herein may be used to selectively apply the protective coating or other active area materials with high precision. During these methods, the bonding region remains free of the active area materials and/or the protective coating, and thus the methods may reduce material waste.

One example of these methods comprises positioning a substrate, having a feature defined therein, with respect to a nozzle of a precision dispense tool such that an air gap between a surface of the substrate and a surface of the nozzle ranges from greater than 0 µm to about 100 µm; and dispensing i) an aqueous hydrogel solution, ii) a pre-grafted aqueous hydrogel solution, or iii) a water-soluble protective coating solution from the nozzle into the feature at a flow rate ranging from about 0.15 µL/s to about 20 µL/s, whereby the surface of the substrate surrounding the feature remains free of i) the aqueous hydrogel solution, ii) the pre-grafted aqueous hydrogel solution, or iii) the water-soluble protective coating solution.

In one instance, the nozzle is a stainless steel conical nozzle. In this instance, the example method may further comprise maintaining the stainless steel conical nozzle in water before and after the dispensing. Also in this instance, the stainless steel conical nozzle may have a gauge ranging from about 17 to about 30. Yet further in this instance, the stainless steel conical nozzle may be coated with a hydrophobic layer.

In another instance, the dispensing is performed to form a layer of the i) the aqueous hydrogel solution, ii) the pre-grafted aqueous hydrogel solution, or iii) the water-soluble protective coating solution having a thickness of about 10 µm or less.

In yet another instance, the precision dispense tool is operated at a linear gantry speed ranging from about 75 mm/s to about 350 mm/s.

It is to be understood that any features of this example method may be combined together in any desirable manner. Moreover, it is to be understood that any combination of features of this example method and any of the first, second, and/or third example methods may be used together, and/or may be combined with any of the examples disclosed herein to achieve the benefits as described in this disclosure, including, for example, forming a flow cell substrate with a precisely applied protective coating and a bonding region free of the protective coating.

Any of the example methods disclosed herein may be used to generate a flow cell. In one instance, the flow cell includes a substrate; a plurality of functionalized pads on the substrate and isolated from each other by interstitial regions, each of the plurality of functionalized pads including: a polymeric hydrogel; and primers attached to the polymeric hydrogel; and a protective coating over the plurality of functionalized pads and not over the interstitial regions.

It is to be understood that any features of the flow cell may be combined together in any desirable manner. Moreover, it is to be understood that any combination of features of the flow cell and/or any of the methods may be used together, and/or may be combined with any of the examples disclosed herein to achieve the benefits as described in this disclosure, including, for example, precisely applied surface chemistry and/or a precisely applied protective coating.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 1A is a top view of an example flow cell;

FIG. 1B through FIG. 1D are enlarged, and partially cutaway views of different examples of the architecture in a flow channel of the flow cell;

FIG. 4A through FIG. 4G are schematic views that illustrate several example methods to apply a protective coating to active areas of a substrate and generate a bonding region that is free of the protective coating;

FIG. 12 is a grey scale fluorescence image of a wafer having an example of a pre-grafted hydrogel selectively applied to the lanes thereof via an example of the methods disclosed herein and after a quality control method was performed, where the lighter color represents low fluorescence intensity and the darker color represents high fluorescence intensity;

FIG. 13A is a microscopy image of example lanes including a protective coating deposited by an example of the methods disclosed herein; and FIG. 13B and FIG. 13C are fluorescence images taken on a microscope (at different magnifications) of comparative example lanes including a protective coating deposited by a comparative method.

DETAILED DESCRIPTION

Figure 2A:
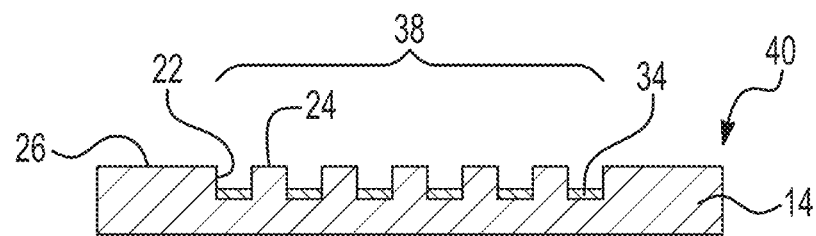
FIG. 2A through FIG. 2D are schematic views that illustrate several example methods to apply a protective coating to active areas of a substrate and generate a bonding region that is free of the protective coating.

Flow cells used in nucleic acid sequencing may include one or more substrates having active areas where amplification, cluster generation, and sequencing can take place. The substrate may be bonded to a lid or to another substrate, e.g., at a bonding region, to create a flow channel for delivering reagents to the active areas. It is generally desirable for the bonding region to be free of the materials of the active area. Additionally, it may be desirable for the active areas to be coated with a protective coating prior to amplification, cluster generation, and sequencing.

Some examples of the method disclosed herein enable the simultaneous preparation of i) the protective coating over the active areas of the substrate, and ii) the bonding region, which is free of the protective coating. Other examples of the method disclosed herein may be used to selectively apply the protective coating or other active area materials with high precision.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, adjacent, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

An "acrylamide monomer" is a monomer with the structure

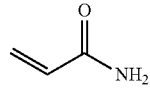

or a monomer including an acrylamide group. Examples of the monomer including an acrylamide group include azido acetamido pentyl acrylamide:

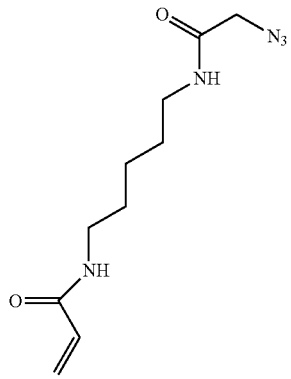 [SMILES: C=CC(=O)NCCCCCNC(=O)CN=[N+]=[N-]]

and N-isopropylacrylamide:

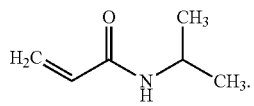

Other acrylamide monomers may be used.

The term "active area" refers to the region of a substrate where a reaction can be carried out. During fabrication of the flow cell, the active area may include a polymeric hydrogel that is capable of attaching primers that can participate in nucleic acid template amplification. In the final flow cell, the active area may include the polymeric hydrogel with the primers attached thereto.

The term "activation," as used herein, refers to a process that generates reactive groups at the surface of a base support or an outermost layer of a multi-layered structure. Activation may be accomplished using silanization or plasma ashing. It is to be understood that activation may be performed in any of the methods disclosed herein. When activation is performed, it is to be understood that a silanized layer or —OH groups (from plasma ashing) are present to covalently attach the polymeric hydrogel to the underlying support or layer.

An "aldehyde," as used herein, is an organic compound containing a functional group with the structure —CHO, which includes a carbonyl center (i.e., a carbon double-bonded to oxygen) with the carbon atom also bonded to hydrogen and an R group, such as an alkyl or other side chain. The general structure of an aldehyde is:

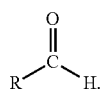

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

An "amino" functional group refers to an —NR$_a$R$_b$ group, where R$_a$ and R$_b$ are each independently selected from hydrogen (e.g., $\overset{\cdot\cdot\cdot}{\diagdown}\diagup^{NH_2}$), C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, the term "attached" refers to the state of two things being joined, fastened, adhered, connected or bound to each other, either directly or indirectly. For example, a nucleic acid can be attached to a polymeric hydrogel by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to —N$_3$.

As used herein, a "bonding region" refers to an area of a substrate that is to be bonded to another material, which may be, as examples, a spacer layer, a lid, another substrate, etc., or combinations thereof (e.g., a spacer layer and a lid, or a spacer layer and another substrate). The bond that is formed at the bonding region may be a chemical bond (as described above), or a mechanical bond (e.g., using a fastener, etc.).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to —COONH As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, the term "depression" refers to a discrete concave feature defined in a substrate and having a surface opening that is at least partially surrounded by interstitial region(s) of the substrate. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells.

The term "each," when used in reference to a collection of items, is intended to identify an individual item in the collection, but does not necessarily refer to every item in the collection. Exceptions can occur if explicit disclosure or context clearly dictates otherwise.

The term "epoxy" (also referred to as a glycidyl or oxirane group) as used herein refers to

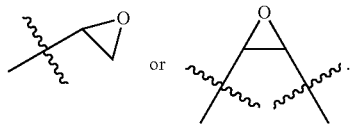

The term "feature" refers to depression or a lane that is at least partially defined by a substrate. In some instances, the feature is defined in a substrate by imprinting, etching, or another suitable technique. In other instances, a feature is defined on a substrate using one or more additional materials that are built up on the substrate surface.

As used herein, the term "flow cell" is intended to mean a vessel having a flow channel where a reaction can be carried out, an inlet for delivering reagent(s) to the flow channel, and an outlet for removing reagent(s) from the flow channel. In some examples, the flow cell accommodates the detection of the reaction that occurs in the flow cell. For example, the flow cell can include one or more transparent surfaces allowing for the optical detection of arrays, optically labeled molecules, or the like.

As used herein, a "flow channel" or "channel" may be an area defined between two bonded components, which can selectively receive a liquid sample. In some examples, the flow channel may be defined between two substrates, and thus may be in fluid communication with the active area(s) of each of the substrates. In other examples, the flow channel may be defined between a substrate and a lid, and thus may be in fluid communication with active area(s) of the substrate.

As used herein, a "functionalized pad" refers to a polymeric hydrogel that i) is positioned on a substrate surface, ii) is isolated from other polymeric hydrogels on the substrate surface by interstitial regions, and iii) has primers attached thereto. The functionalized pad sits on a substantially flat substrate surface.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocycle" means a non-aromatic cyclic ring or ring system containing at least one heteroatom in the ring backbone. Heterocycles may be joined together in a fused, bridged or spiro-connected fashion. Heterocycles may have any degree of saturation provided that at least one ring in the ring system is not aromatic. In the ring system, the heteroatom(s) may be present in either a non-aromatic or aromatic ring. The heterocycle group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

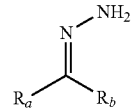

group in which R$_a$ and R$_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocycle, as defined herein.

As used herein, "hydroxy" or "hydroxyl" refers to an —OH group.

As used herein, the term "interstitial region" refers to an area, e.g., of a substrate that separates depressions or functionalized pads. For example, an interstitial region can separate one depression or functionalized pad of an array from another depression or functionalized pad of the array. The depressions or functionalized pads that are separated from each other can be discrete, i.e., lacking physical contact with each other. In many examples, the interstitial region is continuous, whereas the depressions or the functionalized pads are discrete, for example, as is the case for a plurality of depressions or functionalized pads defined in or on an otherwise continuous surface. In other examples, the interstitial regions and the depressions or functionalized pads are discrete, for example, as is the case for a plurality of depressions in the shape of trenches, which are separated by respective interstitial regions. The separation provided by an interstitial region can be partial or full separation. Interstitial regions may have a surface material that differs from the surface material of the depressions or the functionalized pads. For example, depressions can have the polymeric hydrogel and primers therein, and the interstitial regions can be free of both the polymeric hydrogel and primers.

As used herein, a "negative photoresist" refers to a light-sensitive material in which a portion that is exposed to light of particular wavelength(s) becomes insoluble to a developer. In these examples, the insoluble negative photoresist has less than 5% solubility in the developer. With the negative photoresist, the light exposure changes the chemical structure so that the exposed portions of the material becomes less soluble (than non-exposed portions) in the developer. While not soluble in the developer, the insoluble negative photoresist may be at least 95% soluble in a remover that is different from the developer. In some examples, the insoluble negative photoresist is at least 98%, e.g., 99%, 99.5%, 100%, soluble in the remover. The remover may be a solvent or solvent mixture used, e.g., in a lift-off process.

In contrast to the insoluble negative photoresist, any portion of the negative photoresist that is not exposed to light is at least 95% soluble in the developer. In some examples, the portion of the negative photoresist not exposed to light is at least 98%, e.g., 99%, 99.5%, 100%, soluble in the developer.

"Nitrile oxide," as used herein, means a "$R_aC\equiv N^+O^-$" group in which $R_a$ is defined herein. Examples of preparing nitrile oxide include in situ generation from aldoximes by treatment with chloramide-T or through action of base on imidoyl chlorides [RC(Cl)=NOH] or from the reaction between hydroxylamine and an aldehyde.

"Nitrone," as used herein, means a

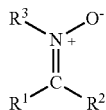

group in which $R^1$, $R^2$, and $R^3$ may be any of the $R_a$ and $R_b$ groups defined herein, except that $R^3$ is not hydrogen (H).

A "non-patterned structure" refers to a substrate having one continuous active area. As an example, the active area may extend along the entire length of a lane defined in the substrate, but is not present in depressions or as functionalized pads that are positioned in a defined pattern.

As used herein, a "nucleotide" includes a nitrogen containing heterocyclic base, a sugar, and one or more phosphate groups. Nucleotides are monomeric units of a nucleic acid sequence. In RNA (ribonucleic acid), the sugar is a ribose, and in DNA (deoxyribonucleic acid), the sugar is a deoxyribose, i.e., a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

In some examples, the term "over" may mean that one component or material is positioned directly on another component or material. When one is directly on another, the two are in contact with each other. In FIG. 1B, the layer 16 is applied over the base support 14 so that it is directly on and in contact with the base support 14.

In other examples, the term "over" may mean that one component or material is positioned indirectly on another component or material. By indirectly on, it is meant that a gap or an additional component or material may be positioned between the two components or materials. In FIG. 1B, the protective coating 20 is positioned over the base support 14 such that the two are in indirect contact. More specifically, the protective coating 20 is indirectly over the base support 14 because the layer 16 is positioned between the two components 14 and 20.

A "patterned resin" refers to any polymer that can have depressions defined therein. Specific examples of resins and techniques for patterning the resins will be described further below.

A "patterned structure" refers to a substrate that includes the active area material(s) in a pattern, e.g., in depressions or as functionalized pads. In some examples, the substrate is exposed to patterning techniques (e.g., etching, lithography, etc.) in order to generate the pattern for the active areas. However, the term "patterned structure" is not intended to imply that such patterning techniques have to be used to generate the pattern. For example, a substrate may be a substantially flat surface having a pattern of the functionalized pads thereon. The patterned structure may be generated via any of the methods disclosed herein.

The term "polymeric hydrogel" refers to a semi-rigid polymer that is permeable to liquids and gases. The polymeric hydrogel can swell when liquid (e.g., water) is taken up and that can contract when liquid is removed, e.g., by drying. While a hydrogel may absorb water, it is not water-soluble.

As used herein, a "positive photoresist" refers to a light-sensitive material in which a portion that is exposed to light of particular wavelength(s) becomes soluble to a developer. In these examples, any portion of the positive photoresist exposed to light is at least 95% soluble in the developer. In some examples, the portion of the positive photoresist exposed to light is at least 98%, e.g., 99%, 99.5%, 100%, soluble in the developer. With the positive photoresist, the light exposure changes the chemical structure so that the exposed portions of the material become more soluble (than non-exposed portions) in the developer.

In contrast to the soluble positive photoresist, any portion of the positive photoresist not exposed to light is insoluble (less than 5% soluble) in the developer. While not soluble in the developer, the insoluble positive photoresist may be at least 95% soluble in a remover that is different from the developer. In some examples, insoluble positive photoresist is at least 98%, e.g., 99%, 99.5%, 100%, soluble in the remover. The remover may be a solvent or solvent mixture used in a lift-off process.

As used herein, the "primer" is defined as a single stranded nucleic acid sequence (e.g., single stranded DNA). Some primers, referred to herein as amplification primers, serve as a starting point for template amplification and cluster generation. Other primers, referred to herein as sequencing primers, serve as a starting point for DNA synthesis. The 5' terminus of the primer may be modified to allow a coupling reaction with a functional group of a polymeric hydrogel. The primer length can be any number of bases long and can include a variety of non-natural nucleotides. In an example, the sequencing primer is a short strand, ranging from 10 to 60 bases, or from 20 to 40 bases.

As used herein, the term "protective coating" refers to a water-soluble material in the form of a solid (e.g., a thin film), or a gel, or a liquid that is applied on the active area of a substrate. The protective coating may be any water-soluble material that does not deleteriously affect the underlying surface chemistry or substrate and that serves to protect and/or preserve the functionality of the active area. A water-soluble protective coating is, by definition, distinguishable from a polymeric hydrogel, as the protective coating dissolves when exposed to water, and may be washed away in this manner; while the polymeric hydrogel is water-insoluble. The protective coating may swell the polymeric hydrogel and at least substantially prevent the layer from undergoing deleterious changes during processing and/or shipping and/or storage. For another example, the protective coating may preserve the accessibility of the primer and at least substantially prevent degradation of the polymeric hydrogel.

A "spacer layer," as used herein refers to a material that bonds two components together. In some examples, the spacer layer can be a radiation-absorbing material that aids in bonding, or can be put into contact with a radiation-absorbing material that aids in bonding.

The term "substrate" refers to the single layer base support or a multi-layer structure upon which the active area is introduced.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refers to five-membered heterocyclic group including four nitrogen atoms. Tetrazole can be optionally substituted.

The term "transparent" when describing a material (e.g., substrate, layer, etc.) means that that the material allows light of a particular wavelength or range of wavelengths to pass through. For example, the material may be transparent to wavelength(s) that are used to chemically change a negative photoresist. Transparency may be quantified using transmittance, i.e., the ratio of light energy falling on a body to that transmitted through the body. The transmittance of a transparent material will depend upon the thickness of the material and the wavelength of light. In the examples disclosed herein, the transmittance of the transparent material may range from 0.25 (25%) to 1 (100%). The material may be a pure material, a material with some impurities, or a mixture of materials, as long as the resulting material is capable of the desired transmittance. Additionally, depending upon the transmittance of the material, the time for light exposure and/or the output power of the light source may be increased or decreased to deliver a suitable dose of light energy through the transparent material to achieve the desired effect (e.g., generating an insoluble photoresist).

Protective Coating

Examples of the method disclosed herein may be used to apply the protective coating over active area(s) of the substrate. While the details of each method are provided herein in reference to the FIG. 2 series through the FIG. 9 series, the application of the protective coating generally involves an aqueous solution of a water-soluble protective material that is deposited and left wet, or is deposited and dried (e.g., by warming, heating, evaporation, vacuum exposure, convective drying, or the like). The aqueous solution is referred to herein as the water-soluble protective coating solution. In some examples, the water-soluble protective coating solution includes up to about 15%, or about 1 to 15%, or about 1 to 10%, or about 1 to 5%, or about 2 to 5%, or about 4 to 8%, or about 5 to 7.5%, or about 5%, or about 7.5% (mass to volume), of the water-soluble protective material. In some examples, the water-soluble protective coating solution includes from about 5 to about 7.5%, or about 5%, or 7.5% (mass to volume) of the water-soluble protective material.

In addition to water, some examples of the water-soluble protective coating solution may include an alcohol co-solvent to increase the drying rate and decrease the surface tension. Other suitable co-solvents may include low volatility solvents, such as glycerol, to slow down evaporation.

In some examples, the protective coating is at least 95% soluble (e.g., 98%, 99%, 100%) in water so it can be readily removed from the active area(s) prior to amplification and clustering. Examples of the water-soluble protective material that may be used to generate this type of protective coating include polyvinyl alcohol, a polyvinyl alcohol/polyethylene glycol graft copolymer (e.g., KOLLICOAT® IR, available from BASF Corp.), sucrose, chitosan, dextran (e.g., molecular weight of 200,000 Da), polyacrylamide (e.g., molecular weight of 40,000 Da, 200,000 Da, etc.), polyethylene glycol, ethylenediaminetetraacetic acid sodium salt (i.e., EDTA), tris(hydroxymethyl)aminomethane with ethylenediaminetetraacetic acid, (tris(2-carboxyethyl)phosphine), tris(3-hydroxypropyltriazolylmethyl) amine, bathophenanthrolinedisulfonic acid disodium salt, hydroxyl functional polymers, glycerol, and saline sodium citrate. Any of these water-soluble protective materials may be used in the methods disclosed herein that apply the protective coating with high precision to the active area(s), but not to the bonding region. Any of these water-soluble protective materials, except for polyethylene glycol, may also be used in the methods disclosed herein that dry etch or ablate portions of the protective coating rather than exposing them to insoluble negative photoresist removers.

In other examples, the protective coating is at least 95% soluble in water and is also at least 95% insoluble in a remover that is used during the method, for example, to remove an insoluble positive or negative photoresist. Examples of the water-soluble protective material that may be used to generate this type of protective coating include polyvinyl alcohol, a polyvinyl alcohol/polyethylene glycol graft copolymer (e.g., KOLLICOAT® IR, available from BASF Corp.), sucrose, chitosan, dextran (e.g., molecular weight of 200,000 Da), and glycerol. Any of these protective coating materials may be used in the methods that utilize a positive or negative photoresist and a remover.

Flow Cells

Examples of the method disclosed herein may be used in the preparation of a flow cell. The flow cell includes at least one patterned structure or at least one non-patterned structure.

One example of the flow cell 10 is shown in FIG. 1A from a top view. The flow cell 10 may include two patterned structures bonded together, two non-patterned structures bonded together, or one patterned or non-patterned structure bonded to a lid. Between the two patterned or non-patterned structures, or between the one patterned or non-patterned structure and the lid is a flow channel 12. The example shown in FIG. 1A includes eight flow channels 12. While eight flow channels 12 are shown, it is to be understood that any number of flow channels 12 may be included in the flow cell 10 (e.g., a single flow channel 12, four flow channels 12, etc.). Each flow channel 12 may be isolated from another flow channel 12 so that fluid introduced into a flow channel 12 does not flow into adjacent flow channel(s) 12. Some examples of the fluids introduced into the flow channel 12 may introduce reaction components (e.g., DNA sample, polymerases, sequencing primers, nucleotides, etc.), washing solutions, deblocking agents, etc.

The flow channel 12 is at least partially defined by a patterned structure or a non-patterned structure. The patterned or non-patterned structure may include a substrate, such as a single layer base support 14 (as shown in FIG. 1C), or a multi-layered structure 18 (as shown in FIGS. 1B and 1D).

Examples of suitable single layer base supports 14 include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HfO_2$), carbon, metals, inorganic glasses, or the like.

Examples of the multi-layered structure 18 include the base support 14 and at least one other layer 16 thereon, as shown in FIG. 1B and FIG. 1D. Some examples of the multi-layered structure 18 include glass or silicon as the base support 14, with a coating layer (e.g., layer 16) of tantalum oxide (e.g., tantalum pentoxide or another tantalum oxide(s) ($TaO_x$)) or another ceramic oxide at the surface.

Other examples of the multi-layered structure 18 include the base support 14 (e.g., glass, silicon, tantalum pentoxide, or any of the other base support 14 materials) and a patterned resin as the other layer 16. It is to be understood that any material that can be selectively deposited, or deposited and patterned to form depressions 22 and interstitial regions 24 may be used for the patterned resin.

As one example, an inorganic oxide may be selectively applied to the base support 14 via vapor deposition, aerosol printing, or inkjet printing to generate the patterned resin. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), and/or combinations thereof or other mixed metal oxides.

As another example, a polymeric resin may be applied to the base support 14 and then patterned to generate the patterned resin. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, etc. Some examples of suitable resins include a polyhedral oligomeric silsesquioxane-based resin, a non-polyhedral oligomeric silsesquioxane epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (an example of which is commerically available under the tradename "POSS") refers to a chemical composition that is a hybrid intermediate (e.g., $RSiO_{1.5}$) between that of silica ($SiO_2$) and silicone ($R_2SiO$). An example of polyhedral oligomeric silsesquioxane may be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups.

Still other examples of the multi-layered structure 18 include a transparent base support 14' (see FIG. 6B for example); a patterned mask layer 48 (see FIG. 6B) over the transparent base support 14'; and a transparent layer 16' (see FIG. 6B) over the patterned mask layer 48. While the single layer base support 14 is shown and referenced in FIG. 1B through FIG. 1D, it is to be understood that the description is also applicable to the transparent base support 12'.

The single layer base support 14 (whether used singly or as part of the multi-layered structure 18) may be a circular sheet, a panel, a wafer, a die etc. having a diameter ranging from about 2 mm to about 300 mm, e.g., from about 200 mm to about 300 mm, or may be a rectangular sheet, panel, wafer, die etc. having its largest dimension up to about 10 feet (~3 meters). For example, a die may have a width ranging from about 0.1 mm to about 10 mm. While example dimensions have been provided, it is to be understood that a single base support 14 with any suitable dimensions may be used.

In an example, the flow channel 12 has a rectangular configuration. The length and width of the flow channel 12 may be selected so a portion of the single base support 14 or an outermost layer of the multi-layered structure 18 surrounds the flow channel 12 and is available for attachment to a lid (not shown) or another patterned or non-patterned structure. The surrounding portions are the bonding regions 26.

The depth of the flow channel 12 can be as small as a monolayer thick when microcontact, aerosol, or inkjet printing is used to deposit a separate material over the bonding region 26 that defines the flow channel 12 walls. In other examples, a thicker spacer layer may be applied to bonding region 26 so that the spacer layer defines at least a portion of the walls of the flow channel 12. As one example, the spacer layer can be a radiation-absorbing material that aids in bonding. In these examples, the depth of the flow channel 12 can be about 1 µm, about 10 µm, about 50 µm, about 100 µm, or more. In an example, the depth may range from about 10 µm to about 100 µm. In another example, the depth may range from about 10 µm to about 30 µm. In still another example, the depth is about 5 µm or less. It is to be understood that the depth of the flow channel 12 may be greater than, less than or between the values specified above.

FIG. 1B, FIG. 1C, and FIG. 1D depict examples of the architecture within the flow channel 12. The architecture shown in FIG. 1B is a patterned structure that includes depressions 22 defined in the layer 16 of the multi-layer structure 18, or alternatively, in the single base support 14. The architecture shown in FIG. 1C is a patterned structure that includes functionalized pads 28 defined on the single base support 14, or alternatively, on the layer 16 of the multi-layer structure 18. The architecture shown in FIG. 1D is a non-patterned structure that includes a single lane 30 defined in the layer 16 of the multi-layer structure 18, or alternatively, in the single layer base support 14.

For the patterned structure, many different layouts of the depressions 22 or functionalized pads 28 may be envisaged, including regular, repeating, and non-regular patterns. In an example, the depressions 22 or functionalized pads 28 are disposed in a hexagonal grid for close packing and improved density. Other layouts may include, for example, rectilinear (rectangular) layouts, triangular layouts, and so forth. In some examples, the layout or pattern can be an x-y format in rows and columns. In other examples, the layout or pattern can be a repeating arrangement of depressions 22 or functionalized pads 28 and the interstitial regions 24. In still other examples, the layout or pattern can be a random arrangement of the depressions 22 or functionalized pads 28 and the interstitial regions 24.

The layout or pattern may be characterized with respect to the density (number) of the depressions 22 or functionalized pads 28 in a defined area. For example, the depressions 22 or functionalized pads 28 may be present at a density of approximately 2 million per mm$^2$. The density may be tuned to different densities including, for example, a density of about 100 per mm$^2$, about 1,000 per mm$^2$, about 0.1 million per mm$^2$, about 1 million per mm$^2$, about 2 million per mm$^2$, about 5 million per mm$^2$, about 10 million per mm$^2$, about 50 million per mm$^2$, or more, or less. It is to be further understood that the density can be between one of the lower values and one of the upper values selected from the ranges above, or that other densities (outside of the given ranges) may be used. As examples, a high density array may be characterized as having the depressions 22 or functionalized pads 28 separated by less than about 100 nm, a medium density array may be characterized as having the depressions 22 or functionalized pads 28 separated by about 400 nm to about 1 μm, and a low density array may be characterized as having the depressions 22 or functionalized pads 28 separated by greater than about 1 μm.

The layout or pattern of the depressions 22 or functionalized pads 28 may also or alternatively be characterized in terms of the average pitch, or the spacing from the center of one depression 22 or functionalized pad 28 to the center of an adjacent depression 22 or functionalized pad 28 (center-to-center spacing) or from the right edge of one depression 22 or functionalized pad 28 to the left edge of an adjacent depression 22 or functionalized pad 28 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 μm, about 0.5 μm, about 1 μm, about 5 μm, about 10 μm, about 100 μm, or more or less. The average pitch for a particular pattern of can be between one of the lower values and one of the upper values selected from the ranges above. In an example, the depressions 22 have a pitch (center-to-center spacing) of about 1.5 μm. While example average pitch values have been provided, it is to be understood that other average pitch values may be used.

The size of each depression 22 may be characterized by its volume, opening area, depth, and/or diameter or length and width. For example, the volume can range from about 1×10$^{-3}$ μm$^3$ to about 100 μm$^3$, e.g., about 1×10$^{-2}$ μm$^3$, about 0.1 μm$^3$, about 1 μm$^3$, about 10 μm$^3$, or more, or less. For another example, the opening area can range from about 1×10$^{-3}$ μm$^2$ to about 100 μm$^2$, e.g., about 1×10$^{-2}$ μm$^2$, about 0.1 μm$^2$, about 1 μm$^2$, at least about 10 μm$^2$, or more, or less. For still another example, the depth can range from about 0.1 μm to about 100 μm, e.g., about 0.5 μm, about 1 μm, about 10 μm, or more, or less. For another example, the depth can range from about 0.1 μm to about 100 μm, e.g., about 0.5 μm, about 1 μm, about 10 μm, or more, or less. For yet another example, the diameter or each of the length and width can range from about 0.1 μm to about 100 μm, e.g., about 0.5 μm, about 1 μm, about 10 μm, or more, or less.

The size of each functionalized pad 28 may be characterized by its top surface area, height, and/or diameter or length and width. In an example, the top surface area can range from about 1×10$^{-3}$ μm$^2$ to about 100 μm$^2$, e.g., about 1×10$^{-2}$ μm$^2$, about 0.1 μm$^2$, about 1 μm$^2$, at least about 10 μm$^2$, or more, or less. For still another example, the height can range from about 0.1 μm to about 100 μm, e.g., about 0.5 μm, about 1 μm, about 10 μm, or more, or less. For yet another example, the diameter or each of the length and width can range from about 0.1 μm to about 100 μm, e.g., about 0.5 μm, about 1 μm, about 10 μm, or more, or less.

For the non-patterned structure, the lane 30 may have the same configuration as the flow channel 12.

Each of the architectures also includes the active area 32. The active area 32 includes the polymeric hydrogel 34 and primers 36A, 36B. In the patterned structure of FIG. 1B, the active area 32 is located within the depression 22. In the patterned structure of FIG. 1C, the active area 32 is the functionalized pad 28. In the non-patterned structure of FIG. 1D, the active area 32 extends along the lane 30.

The polymeric hydrogel 34 may be any gel material that can swell when liquid is taken up and can contract when liquid is removed, e.g., by drying. In an example, the polymeric hydrogel 34 includes an acrylamide copolymer, such as poly(N-(5-azidoacetamidylpentyl)acrylamide-co-acrylamide, PAZAM. PAZAM and some other forms of the acrylamide copolymer are represented by the following structure (I):

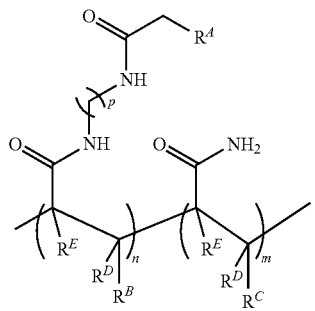

wherein:

$R^A$ is selected from the group consisting of azido, optionally substituted amino, optionally substituted alkenyl, optionally substituted alkyne, halogen, optionally substituted hydrazine, optionally substituted hydrazine, carboxyl, hydroxy, optionally substituted tetrazole, optionally substituted tetrazine, nitrile oxide, nitrone, sulfate, and thiol;

$R^B$ is H or optionally substituted alkyl;

$R^C$, $R^D$, and $R^E$ are each independently selected from the group consisting of H and optionally substituted alkyl;

each of the —$(CH_2)_p$— can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of PAZAM and other forms of the acrylamide copolymer may range from about 5 kDa to about 1500 kDa or from about 10 kDa to about 1000 kDa, or may be, in a specific example, about 312 kDa.

In some examples, PAZAM and other forms of the acrylamide copolymer are linear polymers. In some other examples, PAZAM and other forms of the acrylamide copolymer are lightly cross-linked polymers.

In other examples, the gel material may be a variation of the structure (I). In one example, the acrylamide unit may be replaced with N,N-dimethylacrylamide

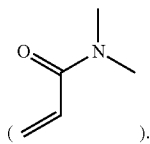

In this example, the acrylamide unit in structure (I) may be replaced with

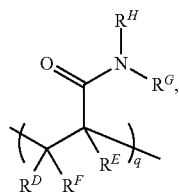

where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

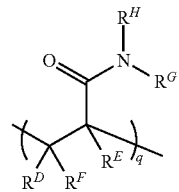

in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

As another example of the polymeric hydrogel 34, the recurring "n" feature in structure (I) may be replaced with a monomer including a heterocyclic azido group having structure (II):

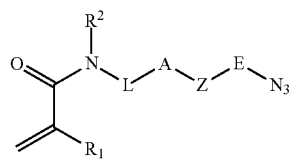

wherein $R^1$ is H or a C1-C6 alkyl; $R_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 carbon-containing ring members present as a single cyclic structure or a fused structure. Some specific examples of Z include pyrrolidinyl, pyridinyl, or pyrimidinyl.

As still another example, the polymeric hydrogel 34 may include a recurring unit of each of structure (III) and (IV):

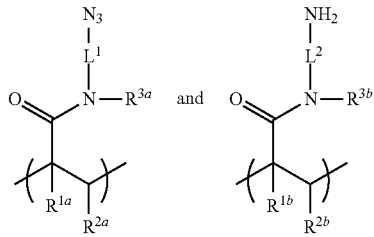

wherein each of $R^{1a}$, $R^{2a}$, $R^{1b}$ and $R^{2b}$ is independently selected from hydrogen, an optionally substituted alkyl or optionally substituted phenyl; each of $R^{1a}$ and $R^{1b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

It is to be understood that other polymeric hydrogels 34 may be used, as long as they are functionalized to graft oligonucleotide primers 36A, 36B thereto. Some examples of suitable the polymeric hydrogel 34 include functionalized polysilanes, such as norbornene silane, azido silane, alkyne functionalized silane, amine functionalized silane, maleimide silane, or any other polysilane having functional groups that can attach the desired primer set 36A, 36B. Other examples of suitable polymeric hydrogels 34 include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymeric hydrogels include mixed copolymers of acrylamides and acrylates. A variety of polymer architectures containing acrylic monomers (e.g., acrylamides, acrylates etc.) may be utilized in the examples disclosed herein, such as branched polymers, including dendrimers, and the like. For example, the monomers (e.g., acrylamide, etc.) may be incorporated, either randomly or in block, into the branches (arms) of a dendrimer.

The polymeric hydrogel 34 may be formed using any suitable copolymerization process. The polymeric hydrogel 34 may be deposited using any of the methods disclosed herein. For at least some of the deposition techniques, the polymeric hydrogel 34 may be incorporated into a mixture, e.g., with water or with ethanol and water, and then applied.

The attachment of the polymeric hydrogel 34 to the underlying base support 14 or layer 16 (e.g., a metal oxide coating, a resin, etc.) of the multi-layer structure 18 may be through covalent bonding. In some instances, the underlying base support 14 or layer 16 may first be activated, e.g., through silanization or plasma ashing. Covalent linking is helpful for maintaining the primers 36A, 36B in the active area 32 throughout the lifetime of the flow cell 10 during a variety of uses.

Each of the architectures also includes the primer 36A, 36B attached to the polymeric hydrogel 34.

A grafting process may be performed to graft the amplification primers 36A, 36B to the polymeric hydrogel 34 either before or after it is deposited in accordance with the examples set forth herein. In an example, the amplification primers 36A, 36B can be immobilized to the polymeric hydrogel 34 by single point covalent attachment at or near the 5' end of the primers 36A, 36B. This attachment leaves i) an adapter-specific portion of the primers 36A, 36B free to anneal to its cognate sequencing-ready nucleic acid fragment and ii) the 3' hydroxyl group free for primer extension. Any suitable covalent attachment may be used for this purpose. Examples of terminated primers that may be used include alkyne terminated primers (e.g., which may attach to an azide surface moiety of the polymeric hydrogel 34), or azide terminated primers (e.g., which may attach to an alkyne surface moiety of the polymeric hydrogel 34), or phospho-thioate terminated primers (e.g., which may attach to a bromine surface moiety of the polymeric hydrogel 34).

Specific examples of suitable primers 36A, 36B include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms.

Primer grafting may be performed before or after the polymeric hydrogel 34 is applied on the substrate. In an example, grafting may involve flow through deposition, dunk coating, spray coating, puddle dispensing, or by another suitable method that will attach the primer(s) 36A, 36B to the polymeric hydrogel 34. Each of these example techniques may utilize a primer solution or mixture, which may include the primer(s) 36A, 36B, water, a buffer, and a catalyst. With any of the grafting methods, the primers 36A, 36B react with reactive groups of the polymeric hydrogel 34. When the primers 36A, 36B are grafted after the polymeric hydrogel 34 has been applied to the substrate, it is to be understood that the primers 36A, 36B have no affinity for the interstitial regions 22 of the bonding region 26. As such, the primers 36A, 36B selectively graft to the polymeric hydrogel 34.

In the examples shown in FIG. 1B, FIG. 1C, and FIG. 1D, the flow cell 10 also includes the protective coating 20. Any example of the water-soluble protective coating solution may be applied to form the protective coating 20. Example methods for generating the protective coating 20 will be now be described.

Protective Coating Patterning Methods

Several example methods for applying the protective coating 20 are shown in reference to the FIG. 2 series through the FIG. 9 series. Each of these methods results in the protective coating 20 applied over the active areas 32 and not applied over the bonding region 26. During these methods, the active areas 32 may be continuously hydrated or coated, which protects the surface chemistry, including the polymeric hydrogel 34 and/or the primers 36A, 36B, from degradation due, for example, to processing conditions such as drying.

Each of the methods shown in the FIG. 2 series through the FIG. 7 series generally includes applying a water-soluble protective coating solution over the bonding region 26 and either i) a patterned region 38 of a patterned structure 40, the patterned region 38 including depressions 22 having at least a polymeric hydrogel 34 therein, and interstitial regions 24 separating the depressions 22, or ii) a lane region of a non-patterned structure, the lane region include a lane 30 having at least a polymeric hydrogel 34 therein; drying the water-soluble protective coating solution to form a solid coating or a gel coating (both of which are examples of the protective coating 20), over the bonding region 26 and over either i) the patterned region 38 or ii) the lane region; and selectively removing portions of the protective coating 20 from the bonding region 26 while leaving other portions of the protective coating 20 over either i) the patterned region 38 or ii) the lane region.

The methods shown in the FIG. 2 series through the FIG. 6 series and the FIG. 8 series depict the patterned structure 40 with depressions 22 and interstitial regions 24 in the patterned region 38. It is to be understood that each of these methods may be performed with the non-patterned structure, e.g., as shown in FIG. 1D, instead of the patterned structure. The methods are performed in the same manner as described herein, except that the patterned region 38 would be replaced with the lane region (e.g., lane 30) so that the polymeric hydrogel 34, the primers 36A, 36B, and the protective coating 20 would be over the lane 30 and not over the surrounding bonding region 26.

Figure 2B:
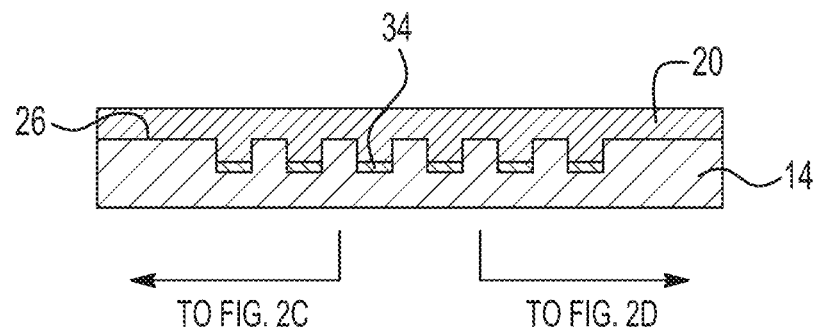
Figure 2C:
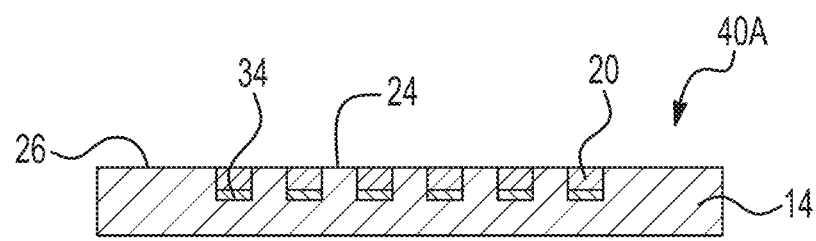
Figure 2D:
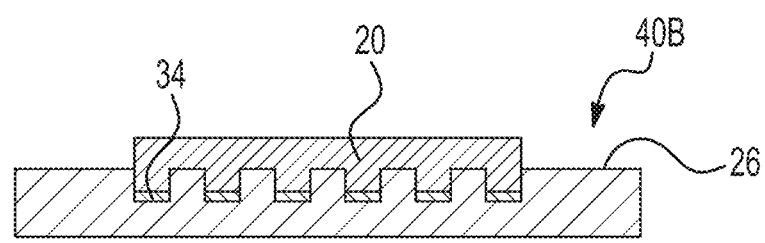

FIG. 2A through FIG. 2D illustrate multiple different examples of the method. In particular, FIG. 2A, FIG. 2B, and FIG. 2C illustrate one example method, and FIG. 2A, FIG. 2B, and FIG. 2D illustrate another example method.

As shown in FIG. 2A, the substrate of the patterned structure 40 is a single layer base support 14 with the depressions 22 defined in one surface of the single layer base support 14. The depressions 22 may be defined via etching, imprinting, lithography, or another suitable technique. While the single layer base support 14 is depicted, it is to be understood that these example methods may be performed with a multi-layer structure 18, where the depressions 22 are defined in the outermost layer 16 (see FIG. 1B).

At the outset of the methods shown in FIG. 2A to FIG. 2D, the base support 14 or the outermost layer 16 of the multi-layer structure 18 may be activated using silanization or plasma ashing to generate surface groups that can react with the polymeric hydrogel 34.

Silanization involves the application of a silane or silane derivative over the surface of the base support 14 or of the layer 16. The selection of the silane or silane derivative may depend, in part, upon the polymeric hydrogel 34 that is to be applied. Some example silane derivatives include a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo[4.2.1]non-1(8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. Other example silane derivatives include a cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0]non-3-yne). These cycloalkynes can be substituted with any of the R groups described herein. The method used to apply the silane or silane derivative may vary depending upon the silane or silane derivative that is being used. Examples of suitable silanization methods include vapor deposition (e.g., a YES method), spin coating, or other deposition methods.

Plasma ashing generates —OH groups. In some examples, plasma ashing may be performed, and then silanization may be performed.

After activation, the polymeric hydrogel 34 may be applied over the base support 14 or the outermost layer 16 of the multi-layer structure 18. The polymeric hydrogel 34 may be applied using any suitable deposition technique. As examples, depositing may be performed using vapor deposition techniques, coating techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, microcontact printing, or the like. These deposition techniques apply the polymeric hydrogel 34 over the surface of the base support 14 or the outermost layer 16 of the multi-layer structure 18, including in the depressions 22.

The polymeric hydrogel 34 that is positioned over the interstitial regions 24 and the bonding region 26 may be removed, e.g., using a polishing process. The polishing process may be performed with a chemical slurry, which can remove the polymeric hydrogel 34 from the interstitial regions 24 and the bonding region 26 without deleteriously affecting the underlying substrate at those regions 24, 26. An example of the chemical slurry may include abrasive particles, a buffer, a chelating agent, a surfactant, and/or a dispersant. Alternatively, polishing may be performed with a solution that does not include the abrasive particles.

The chemical slurry may be used in a chemical mechanical polishing system to polish the surface of the interstitial regions 24 and the bonding region 26. The polishing head(s)/pad(s) or other polishing tool(s) is/are capable of polishing the polymeric hydrogel 34 that may be present over the interstitial regions 24 and the bonding region 26 while leaving the polymeric hydrogel 34 in the depression(s) 20 at least substantially intact. As an example, the polishing head may be a Strasbaugh ViPRR II polishing head.

Some examples of the method then include applying the water-soluble protective coating solution over the bonding region 26 and the patterned region 38 of the patterned structure 40, and drying the water-soluble protective coating solution to form the protective coating 20, which may be a solid coating or a gel coating depending upon the water-soluble protective material in the solution. Any example of water-soluble protective coating solution disclosed herein may be used in this example. The water-soluble protective coating solution may be applied using dip coating, dunk coating, spin coating, spray coating, ultrasonic spray coating, doctor blade coating, or aerosol printing. Drying may be accomplished via air exposure, nitrogen exposure, vacuum, heating (e.g., in an oven), or spin coating (i.e., spinning until dry). FIG. 2B illustrates the resulting protective coating 20.

FIG. 2C and FIG. 2D illustrate two examples of the patterned structure 40A and 40B after portions of the protective coating 20 are selectively removed from the bonding region 26. As illustrated, other portions of the protective coating 20 remain over the patterned region 38 after the selective removal is performed.

In one example, the selective removal may involve laser patterning the portions of the protective coating 20 (i.e., the solid coating or the gel coating) over the bonding region 26. Laser patterning effectively ablates the portions of the protective coating 20 that overlie the bonding region 26. As such, this technique removes the portions of the protective coating 20 that overlie the bonding region 26, but leaves the portions of the protective coating 20 that overlie the patterned region 38 at least substantially intact. The resulting patterned structure 40B is shown in FIG. 2D.

In another example, the selective removal may involve timed dry etching the protective coating 20 (i.e., the solid coating or the gel coating) until the bonding region 26 is exposed. As examples, the timed dry etch may involve a reactive ion etch (e.g., with $CF_4$) or a 100% $O_2$ plasma etch. The timed dry etching is stopped so that the protective coating 20 remains in the depressions 22, but is removed from the bonding region 26 and the interstitial regions 24. The duration of the timed dry etch depend upon the etch rate of the etching process used, and may vary for different protective coatings 20. The resulting patterned structure 40A is shown in FIG. 2C.

As depicted in both FIG. 2C and FIG. 2D, the methods result in at least part of the patterned region 38 (and thus the active area 32) being coated with the protective coating 20, while the bonding region 26 is free of the protective coating 20. The patterned structures 40A, 40B may then be bonded to other patterned structures 40A, 40B or to a lid at the bonding region 26. The bond that is formed may be a chemical bond, or a mechanical bond (e.g., using a fastener, etc.).

Any suitable technique, such as laser bonding, diffusion bonding, anodic bonding, eutectic bonding, plasma activation bonding, glass frit bonding, or other methods known in the art may be used to bond two patterned structures 40A, 40B or a patterned structure 40A, 40B and a lid together. In an example, the spacer layer may be used to bond two patterned structures 40A, 40B or the patterned structure 40A, 40B and the lid. The spacer layer may be any sealing material, such as a radiation-absorbing material that aids in bonding. The presence of the protective coating 20 may protect any underlying surface chemistry during the bonding process.

If a non-patterned structure is used instead of the patterned structure shown in FIG. 2A through FIG. 2D, the methods would result in the lane 30 (and thus the active area 32) being coated with the polymeric hydrogel 34 and the protective coating 20, while the bonding region 26 is free of the polymeric hydrogel 34 and the protective coating 20. The non-patterned structures may then be bonded to other non-patterned structures or to a lid at the bonding region 26. The bond that is formed may be a chemical bond, or a mechanical bond (e.g., using a fastener, etc.).

While not shown in FIG. 2A through FIG. 2D, these methods also include attaching the primer 36A, 36B to the polymeric hydrogel 34. In some examples, the primers 36A, 36B (not shown in FIG. 2A through FIG. 2D) may be pre-grafted to the polymeric hydrogel 34 and thus will be applied to the substrate when the polymeric hydrogel 34 is applied. Pre-grafted primers are grafted to the polymeric hydrogel 34 after it is polymerized and before it is dispensed onto the substrate. In other examples, the primers 36A, 36B may be grafted after the polymeric hydrogel 34 is deposited and polished, but prior to the application of the protective coating 20 (e.g., at FIG. 2A). In still other examples, the primers 36A, 36B may be grafted after the protective coating 20 is applied and the patterned structure 40A, 40B is bonded to a lid (not shown) or another patterned structure 40A, 40B. In these examples, the protective coating 20 would be removed with water prior to grafting. The water and grafting reagents may be introduced using a flow through process.

Figure 3A:
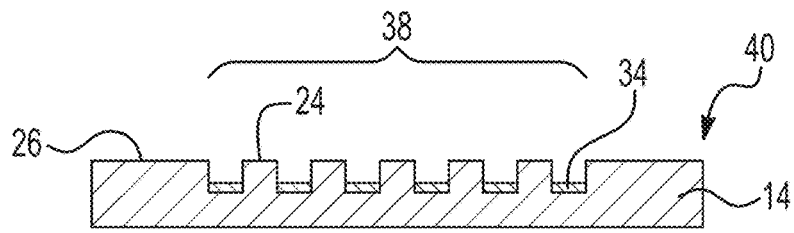
FIG. 3A through FIG. 3E are schematic views that illustrate an example method to apply a protective coating to active areas of a substrate and generate a bonding region that is free of the protective coating.

FIG. 3A through FIG. 3E illustrate another example of the method. As shown in FIG. 3A, the substrate of the patterned structure 40 is a single layer base support 14 with the depressions 22 defined in one surface of the single layer base support 14. The depressions 22 may be defined via etching, imprinting, lithography, or another suitable technique. While the single layer base support 14 is depicted, it is to be understood that this example method may be performed with a multi-layer structure 18, where the depressions 22 are defined in the outermost layer 16 (see FIG. 1B).

At the outset of the method shown in FIG. 3A to FIG. 3E, the base support 14 or the outermost layer 16 of the multi-layer structure 18 may be activated using silanization or plasma ashing to generate surface groups that can react with the polymeric hydrogel 34. After activation, the polymeric hydrogel 34 may be applied over the base support 14 or the outermost layer 16 of the multi-layer structure 18 using any suitable deposition technique. The polymeric hydrogel 34 that is positioned over the interstitial regions 24 and the bonding region 26 may then be removed, e.g., using a polishing process.

Figure 3B:

Some examples of the method then include applying the water-soluble protective coating solution over the bonding region 26 and the patterned region 38 of the patterned structure 40, and drying the water-soluble protective coating solution to form the protective coating 20. Any example of water-soluble protective coating solution disclosed herein may be used in this example. The water-soluble protective coating solution may be applied and dried as described in reference to FIG. 2B. FIG. 3B illustrates the resulting protective coating 20.

In this example method, a metal layer 42 may be applied to the portion of the protective coating 20 that overlies the patterned region 38. The metal layer 42 protects the portion of the protective coating 20 that overlies the patterned region 38 during selective removal of the protective coating 20 from the bonding region 26. In this example, the selective removal process may be performed using a dry etching process, and thus the metal 42 may be any metal that is resistant to the dry etching process. Examples of suitable metals for the metal layer 42 include aluminum, copper, gold, etc. In some examples, the metal may be at least substantially pure (<99% pure). At least substantially pure metals may be used in order to prevent residue on the protective layer 20 after metal layer 42 removal.

Figure 3C:
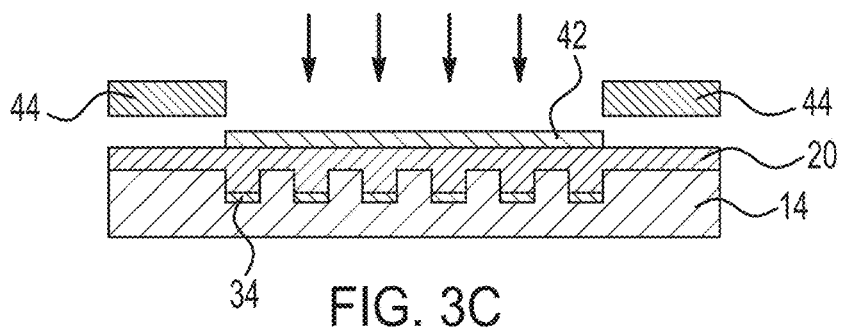

The metal layer 42 may be deposited using a shadow mask 44 and any suitable deposition technique, as depicted in FIG. 3C. The shadow mask 44 is positioned over the bonding region 26 so that the metal layer 42 is not applied to the protective coating 20 that overlies the bonding region 26.

Figure 3D:
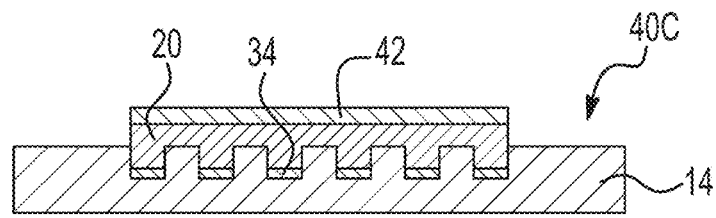

Once the metal layer 42 is in place over the portion of the protective coating 20 that overlies the patterned region 38, dry etching of exposed portions of the protective coating 20 is performed. Dry etching is performed while the metal layer 42 is in place, so that portions of the protective coating 20 overlying the bonding region 26 are removed and portions of the protective coating 20 overlying the patterned region 38 remain at least substantially intact. In one example, dry etching of exposed portions of the protective coating 20 is performed with a pure $O_2$ plasma or a mixture of 10% $CF_4$ and 90% $O_2$ plasma using inductively coupled plasma (ICP) or reactive ion etching (REI). The underlying base support 14 has high resistance to these etching conditions, and thus acts as an etch stop. The patterned structure 40C with the exposed bonding region 26 and the coated patterned region 38 is shown in FIG. 3D (with the metal layer 42 still in place) and in FIG. 3E (with the metal layer 42 removed).

After selectively removing the portions of the solid or gel protective coating 20 that overlie the bonding region 26, the method may further include removing the metal layer 42. This may be performed via metal stripping. As examples, an aluminum metal layer may be stripped using a base solution (e.g., potassium hydroxide (KOH), sodium hydroxide (NaOH), or tetramethylammonium hydroxide (TMAH)), a copper metal layer may be stripped using $FeCl_3$, and a gold metal layer may be stripped using a combination of iodine and potassium iodide.

Figure 3E:
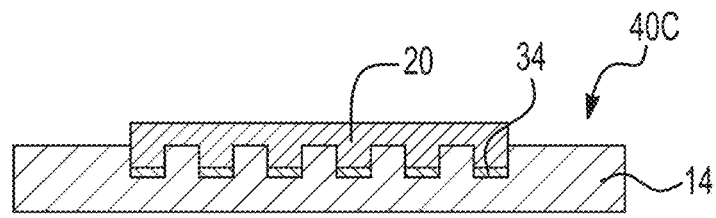

As depicted in FIG. 3E, this method results in the patterned region 38 (and thus the active area 32) being coated with the protective coating 20, while the bonding region 26 is free of the protective coating 20. The patterned structure 40C may be bonded to another patterned structure 40C or to a lid at the bonding region 26. Any suitable bonding technique, such as laser bonding, diffusion bonding, anodic bonding, eutectic bonding, plasma activation bonding, glass frit bonding, or other methods known in the art may be used to bond two patterned structures 40C or a patterned structure 40C and a lid together. In an example, the spacer layer may be used. The presence of the protective coating 20 may protect any underlying surface chemistry during the bonding process.

If a non-patterned structure is used instead of the patterned structure shown in FIG. 3A through FIG. 3E, the methods would result in the lane 30 (and thus the active area 32) being coated with the polymeric hydrogel 34 and the protective coating 20, while the bonding region 26 is free of the polymeric hydrogel 34 and the protective coating 20. The non-patterned structures may then be bonded to other non-patterned structures or to a lid at the bonding region 26. The bond that is formed may be a chemical bond, or a mechanical bond (e.g., using a fastener, etc.).

While not shown in FIG. 3A through FIG. 3E, these methods also include attaching the primer 36A, 36B to the polymeric hydrogel 34. In some examples, the primers 36A, 36B (not shown in FIG. 3A through FIG. 3E) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited and polished, but prior to the application of the protective coating 20 (e.g., at FIG. 3A). In still other examples, the primers 36A, 36B may be grafted after the protective coating 20 is applied, the metal layer 42 is removed, and the patterned structure 40C is bonded to a lid (not shown) or another patterned structure 40C. In these examples, the protective coating 20 would be removed with water prior to grafting. The water and grafting reagents may be introduced using a flow through process.

FIG. 4A through FIG. 4G illustrate multiple examples of the method. In particular, FIG. 4A through FIG. 4E illustrate one example method, and FIG. 4A, FIG. 4F, FIG. 4G, and FIG. 4C through FIG. 4E illustrate another example method.

As shown in FIG. 4A, the substrate is the single layer base support 14 with the depressions 22 defined in one surface of the single layer base support 14. The depressions 22 may be defined via etching, imprinting, lithography, or another suitable technique. While the single layer base support 14 is depicted, it is to be understood that these example methods may be performed with a multi-layer structure 18, where the depressions 22 are defined in the outermost layer 16 (see FIG. 1B).

In each of the example methods shown in the FIG. 4 series, prior to applying the water-soluble protective coating solution, the methods further include applying a photoresist 46 over the bonding region 26 and the patterned region 38 (see FIG. 4B and FIG. 4G), and patterning the photoresist 46 to generate an insoluble photoresist 46' on the bonding region 26 and to remove the (soluble) photoresist 46 from the patterned region 38 (FIG. 4C). If a non-patterned structure is used, the photoresist 46 is applied over the bonding region 26 and the lane region (e.g., lane 30 in FIG. 1D), and the photoresist 46 is patterned to generate an insoluble photoresist 46' on the bonding region 26 and to remove the (soluble) photoresist 46 from the lane region.

In the example method shown in FIG. 4A through FIG. 4E, the photoresist 46 is applied and patterned prior to the polymeric hydrogel 34 being introduced into the depressions 22. This is shown in FIG. 4B.

The photoresist 46 may be a negative photoresist or a positive photoresist.

An example of suitable negative photoresist includes the NR® series photoresist (available from Futurrex). Other suitable negative photoresists include the SU-8 Series and the KMPR® Series (both of which are available from Kayaku Advanced Materials, Inc.), or the UVN™ Series (available from DuPont). When the negative photoresist is used, it is selectively exposed to certain wavelengths of light to form an insoluble photoresist 46', and is exposed to a developer to remove soluble portions (e.g., those portions that are not exposed to the certain wavelengths of light). Examples of suitable developers for the negative photoresist include aqueous-alkaline solutions, such as diluted sodium hydroxide, diluted potassium hydroxide, or an aqueous solution of the metal ion free organic TMAH (tetramethylammonium hydroxide).

Examples of suitable positive photoresists include the MICROPOSIT® S1800 series or the AZ® 1500 series, both of which are available from Kayaku Advanced Materials, Inc. Another example of a suitable positive photoresist is SPR™-220 (from DuPont). The positive photoresist may be applied using any suitable deposition technique disclosed herein. When a positive photoresist is used, selective exposure to certain wavelengths of light form a soluble region (e.g., which is at least 95% soluble in a developer), and the developer is used to remove the soluble regions. Those portions of the positive photoresist not exposed to light will become insoluble in the developer, and thus form the insoluble photoresist 46'. Examples of suitable developers for the positive photoresist include aqueous-alkaline solutions, such as diluted sodium hydroxide, diluted potassium hydroxide, or an aqueous solution of the metal ion free organic TMAH (tetramethylammoniumhydroxide).

In this example, the negative or positive photoresist may be applied and developed so that the portions of the photoresist 46 over the bonding region 26 are insoluble in the developer, and so that the portions of the photoresist 46 over the patterned region 38 are soluble in the developer. A photomask may be used to direct the light (e.g., ultraviolet light) to the appropriate portions, depending upon the type of photoresist 46 that is used. When the negative photoresist is used, the light is directed toward the bonding region 26 to generate the insoluble photoresist 46' and is blocked from the patterned region 38 to generate the soluble photoresist. When the positive photoresist is used, the light is directed toward the patterned region 38 to generate the soluble photoresist and is blocked from the bonding region 26 to generate the insoluble photoresist 46'.

After light exposure, the portion of the photoresist 46 that is soluble in the developer is exposed to the developer, and thus removed. Examples of suitable developers for the negative photoresist include aqueous-alkaline solutions, such as diluted sodium hydroxide, diluted potassium hydroxide, or an aqueous solution of the metal ion free organic TMAH (tetramethylammoniumhydroxide). The soluble portions of the negative photoresist are at least 95% soluble in the developer. Examples of suitable developers for the positive photoresist include aqueous-alkaline solutions, such as diluted sodium hydroxide, diluted potassium hydroxide, or an aqueous solution of the metal ion free organic TMAH (tetramethylammoniumhydroxide). The soluble portions of the positive photoresist are at least 95% soluble in the developer.

FIG. 4C depicts the insoluble photoresist 46' on the bonding region 26 after deposition and development. In this example, after the photoresist 46, 46' is exposed to the developer, the base support 14 may be exposed to an $O_2$ plasma to clean, for example, the depressions 22.

In this example method, after the photoresist 46 is applied and patterned, but before the water-soluble protective coating solution is applied, the method further includes depositing the polymeric hydrogel 34 over the insoluble photoresist 46', the depressions 22, and the interstitial regions 24; and polishing the polymeric hydrogel 34 from the insoluble photoresist 46' and the interstitial regions 24.

Prior to depositing the polymeric hydrogel 34, the exposed portions of the base support 14 or the outermost layer 16 of the multi-layer structure 18 may first be activated using silanization or plasma ashing to generate surface groups that can react with the polymeric hydrogel 34. After activation, the polymeric hydrogel 34 may be applied over the insoluble photoresist 46', the depressions 22, and the interstitial regions 24 using any suitable deposition technique. The polymeric hydrogel 34 that is positioned over the interstitial regions 24 and the bonding region 26 may then be removed, e.g., using a polishing process. After polishing, at least some of the polymeric hydrogel 34 remains in the depressions 22, as shown in FIG. 4C.

As shown in FIG. 4D, this example method then includes applying and drying the water-soluble protective coating solution to form the protective coating 20 over the patterned region 38 and the bonding region 26, and thus over the insoluble photoresist 46'. In these examples, the protective coating 20 is at least 95% soluble in water and is also at least 95% insoluble in the remover that is to be used to remove the insoluble positive or negative photoresist 46'. The water-soluble protective coating solution may be applied and dried as described in reference to FIG. 2B. FIG. 4D illustrates the resulting protective coating 20.

As depicted, the water-soluble protective coating solution is applied over the insoluble photoresist 46', and thus the protective coating 20 is formed over the insoluble photoresist 46'. In this example, selectively removing the portions of the protective coating 20 from the bonding region 26 involves lifting off the insoluble photoresist 46' in a remover. The protective coating 20 is insoluble in the remover. Suitable removers for the insoluble negative photoresist include dimethylsulfoxide (DMSO), acetone, or an NMP (N-methyl-2-pyrrolidone) based stripper. Suitable removers for the insoluble positive photoresist may be dimethylsulfoxide (DMSO), acetone, propylene glycol monomethyl ether acetate, or an NMP (N-methyl-2-pyrrolidone) based stripper. Any of the removers may be used as long as the protective coating 20 is insoluble in it.

As shown in FIG. 4E, the lift-off process removes i) at least 95% of the insoluble photoresist 46' and ii) the protective coating 20 thereon. The other portion of the protective coating 20 remains intact over the patterned region 38. The resulting patterned structure 40D includes the patterned region 38 (and thus the active area 32) being coated with the protective coating 20, while the bonding region 26 is free of the protective coating 20.

The patterned structure 40D may be bonded to another patterned structure 40D or to a lid at the bonding region 26. Any suitable bonding technique, such as laser bonding, diffusion bonding, anodic bonding, eutectic bonding, plasma activation bonding, glass frit bonding, or other methods known in the art may be used to bond two patterned structures 40D or a patterned structure 40D and a lid together. In an example, the spacer layer may be used. The presence of the protective coating 20 may protect any underlying surface chemistry during the bonding process.

If a non-patterned structure is used instead of the patterned structure shown in FIG. 4A through FIG. 4E, the methods would result in the lane 30 (and thus the active area 32) being coated with the polymeric hydrogel 34 and the protective coating 20, while the bonding region 26 is free of the polymeric hydrogel 34 and the protective coating 20. The non-patterned structures may then be bonded to other non-patterned structures or to a lid at the bonding region 26. The bond that is formed may be a chemical bond, or a mechanical bond (e.g., using a fastener, etc.).

While not shown in FIG. 4A through FIG. 4E, this method also includes attaching the primer 36A, 36B to the polymeric hydrogel 34. In some examples, the primers 36A, 36B (not shown in FIG. 4A through FIG. 4E) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited and polished, but prior to the application of the protective coating 20 (e.g., at FIG. 4C). In still other examples, the primers 36A, 36B may be grafted after the protective coating 20 is applied and the patterned structure 40D is bonded to a lid (not shown) or another patterned structure 40D. In these examples, the protective coating 20 would be removed with water prior to grafting. The water and grafting reagents may be introduced using a flow through process.

In the example method shown in FIG. 4A, FIG. 4F, FIG. 4G, and FIG. 4C through FIG. 4E, the photoresist 46 is applied and patterned after the polymeric hydrogel 34 being introduced into the depressions 22. This is shown in FIG. 4G.

This example method moves from FIG. 4A to FIG. 4F, where exposed portions of the base support 14 or the outermost layer 16 of the multi-layer structure 18 may be activated using silanization or plasma ashing. After activation, the polymeric hydrogel 34 may be applied over the base support 14 using any suitable deposition technique. The polymeric hydrogel 34 that is positioned over the interstitial regions 24 and the bonding region 26 may then be removed, e.g., using a polishing process. After polishing, at least some of the polymeric hydrogel 34 remains in the depressions 22, as shown in FIG. 4F.

The photoresist 46 may be applied over the base support 14 and over the polymeric hydrogel 34 in the depressions 22, as shown in FIG. 4G. The photoresist 46 may be developed so that the portions of the photoresist 46 over the bonding region 26 are insoluble in the developer, and so that the portions of the photoresist 46 over the patterned region 38 are soluble in the developer. After suitable light exposure for the type of photoresist 46 being used, the portion of the photoresist 46 that is soluble in the developer is exposed to the developer, and thus removed. The resulting patterned structure 40 is shown in FIG. 4C.

This example method then proceeds to FIG. 4D (application of the protective coating 20) through FIG. 4E (lift-off of the insoluble photoresist 46'), the steps of which are performed as described herein.

If a non-patterned structure is used instead of the patterned structure shown in FIG. 4A, FIG. 4F, FIG. 4G and FIG. 4C through FIG. 4E, the methods would result in the lane 30 (and thus the active area 32) being coated with the polymeric hydrogel 34 and the protective coating 20, while the bonding region 26 is free of the polymeric hydrogel 34 and the protective coating 20. The non-patterned structures may then be bonded to other non-patterned structures or to a lid at the bonding region 26. The bond that is formed may be a chemical bond, or a mechanical bond (e.g., using a fastener, etc.).

While not shown in FIG. 4A, FIG. 4F, FIG. 4G, and FIG. 4C through FIG. 4E, this method also includes attaching the primer 36A, 36B to the polymeric hydrogel 34. In some examples, the primers 36A, 36B (not shown in FIG. 4A through FIG. 4E) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited and polished, but prior to the application of the protective coating 20 (e.g., at FIG. 4F). In still other examples, the primers 36A, 36B may be grafted after the protective coating 20 is applied and the patterned structure 40D is bonded to a lid (not shown) or another patterned structure 40D. In these examples, the protective coating 20 would be removed with water prior to grafting. The water and grafting reagents may be introduced using a flow through process.

Figure 5A:
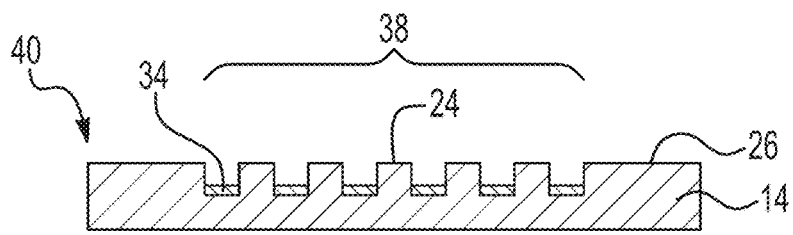
FIG. 5A through FIG. 5E are schematic views that illustrate an example method to apply a protective coating to active areas of a substrate and generate a bonding region that is free of the protective coating.

FIG. 5A through FIG. 5E illustrate another example of the method. As shown in FIG. 5A, the substrate is the single layer base support 14 with the depressions 22 defined in one surface of the single layer base support 14. The depressions 22 may be defined via etching, imprinting, lithography, or another suitable technique. While the single layer base support 14 is depicted, it is to be understood that these example methods may be performed with a multi-layer structure 18, where the depressions 22 are defined in the outermost layer 16 (see FIG. 1B).

At the outset of the method shown in FIG. 5A to FIG. 5E, the base support 14 or the outermost layer 16 of the multi-layer structure 18 may be activated using silanization or plasma ashing to generate surface groups that can react with the polymeric hydrogel 34. After activation, the polymeric hydrogel 34 may be applied over the base support 14 or the outermost layer 16 of the multi-layer structure 18 using any suitable deposition technique. The polymeric hydrogel 34 that is positioned over the interstitial regions 24 and the bonding region 26 may then be removed, e.g., using a polishing process. The patterned structure 40 is shown in FIG. 5A.

Figure 5B:
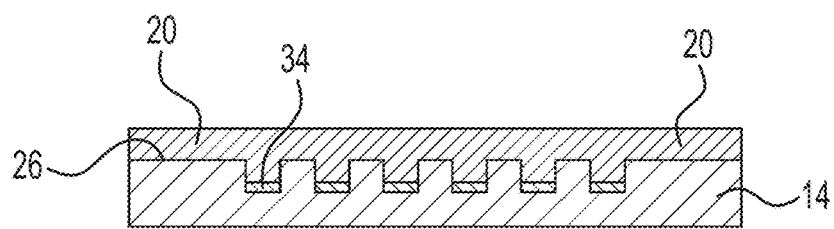
Figure 5C:
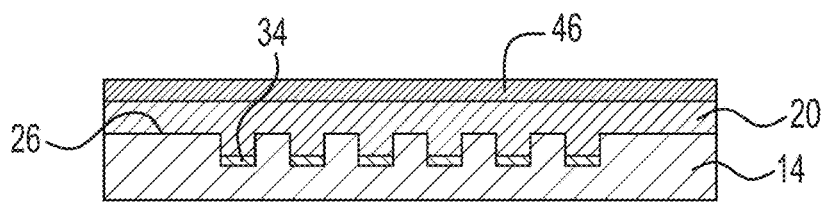

As shown in FIG. 5B, this example method then includes applying and drying the water-soluble protective coating solution to form the protective coating 20 over the patterned region 38 and the bonding region 26. In these examples, the protective coating 20 is at least 95% soluble in water and is also at least 95% insoluble in the remover that is to be used to remove the insoluble positive or negative photoresist 46' that is subsequently developed (see FIG. 5C and FIG. 5D). The water-soluble protective coating solution may be applied and dried as described in reference to FIG. 2B.

In this example method, after drying the water-soluble protective coating solution, the method further includes applying a photoresist 46 over the protective coating 20; and patterning the photoresist 46 to remove the photoresist 46 from the portions of the protective coating 20 over the bonding region 26 and to generate an insoluble photoresist 46' over the other portions of the protective coating 20 over the patterned region 38. If the non-patterned structure is used, the method further includes applying a photoresist 46 over the protective coating 20; and patterning the photoresist 46 to remove the photoresist 46 from the portions of the protective coating 20 over the bonding region 26 and to generate an insoluble photoresist 46' over the other portions of the protective coating 20 over the lane region (e.g., lane 30).

The photoresist 46 may be a negative photoresist or a positive photoresist. In this example, the negative or positive photoresist may be applied and developed so that the portions of the photoresist 46 over the bonding region 26 are soluble in the developer. Also in this example, the negative or positive photoresist may be applied and developed so that the portions of the photoresist 46 over the patterned region 38 are insoluble in the developer. A photomask may be used to direct the light (e.g., ultraviolet light) to the appropriate portions, depending upon the type of photoresist 46 that is used. When the negative photoresist is used, the light is directed toward the patterned region 38 to generate the insoluble photoresist 46' and is blocked from the bonding region 26 to generate the soluble photoresist. When the positive photoresist is used, the light is directed toward the bonding region 26 to generate the soluble photoresist and is blocked from the patterned region 38 to generate the insoluble photoresist 46'.

After light exposure, the portion of the photoresist 46 that is soluble in the developer is exposed to the developer, and thus removed. The developer used depends on the photoresist 46.

Figure 5D:
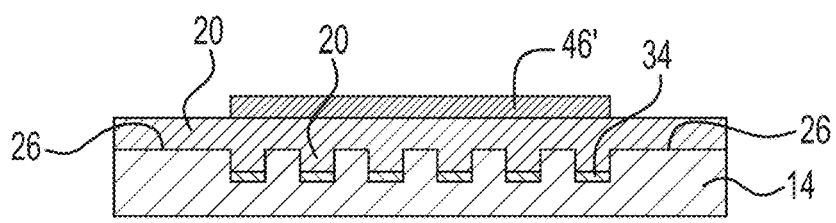

FIG. 5D depicts the insoluble photoresist 46' on the patterned region 38 after deposition and development. As shown, the protective coating 20 overlying the bonding region 26 is exposed.

In this example, the selective removal of the portions of the solid or gel protective coating 20 from the bonding region 26 involves exposing the portions to a dry etch or a water rinse while the insoluble photoresist 46' is in place over the patterned region 38. The dry etching may be performed with a pure $O_2$ plasma or with a mixture of 10% $CF_4$ and 90% $O_2$ plasma using inductively coupled plasma (ICP) or reactive ion etching (REI). The underlying base support 14 has high resistance to these etching conditions, and thus acts as an etch stop. Because the protective coating 20 is soluble in water, the water rinse will dissolve the exposed portions (e.g., those overlying the bonding region 26) and will not affect the portions covered by the insoluble photoresist 46'. As such, the dry etch or water rinse removes the exposed portions of the protective coating 20 from the bonding region 26.

The insoluble photoresist 46' may then be lifted off using a remover. In these examples, the protective coating 20 is selected to be insoluble in the remover, and thus remains at least substantially intact during insoluble photoresist 46' removal. Suitable removers for the insoluble negative photoresist include dimethylsulfoxide (DMSO), acetone, or an NMP (N-methyl-2-pyrrolidone) based stripper. Suitable removers for the insoluble positive photoresist may be dimethylsulfoxide (DMSO), acetone, propylene glycol monomethyl ether acetate, or an NMP (N-methyl-2-pyrrolidone) based stripper. Any of the removers may be used as long as the protective coating 20 is insoluble in it.

Figure 5E:
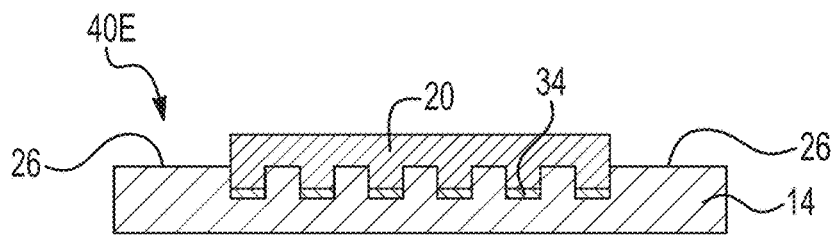

As shown in FIG. 5E, the lift-off process removes at least 95% (e.g., 98%, 99%, 100%) of the insoluble photoresist 46', and thus exposes the underlying protective coating 20. The resulting patterned structure 40E includes the patterned region 38 (and thus the active area 32) being coated with the protective coating 20, while the bonding region 26 is free of the protective coating 20.

The patterned structure 40E may be bonded to another patterned structure 40E or to a lid at the bonding region 26. Any suitable bonding technique, such as laser bonding, diffusion bonding, anodic bonding, eutectic bonding, plasma activation bonding, glass frit bonding, or other methods known in the art may be used to bond two patterned structures 40E or a patterned structure 40E and a lid together. In an example, the spacer layer may be used. The presence of the protective coating 20 may protect any underlying surface chemistry during the bonding process.

If a non-patterned structure is used instead of the patterned structure shown in FIG. 5A through FIG. 5E, the methods would result in the lane 30 (and thus the active area 32) being coated with the polymeric hydrogel 34 and the protective coating 20, while the bonding region 26 is free of the polymeric hydrogel 34 and the protective coating 20. The non-patterned structures may then be bonded to other non-patterned structures or to a lid at the bonding region 26. The bond that is formed may be a chemical bond, or a mechanical bond (e.g., using a fastener, etc.).

While not shown in FIG. 5A through FIG. 5E, this method also includes attaching the primer 36A, 36B to the polymeric hydrogel 34. In some examples, the primers 36A, 36B (not shown in FIG. 5A through FIG. 5E) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited and polished, but prior to the application of the protective coating 20 (e.g., at FIG. 5A). In still other examples, the primers 36A, 36B may be grafted after the protective coating 20 is applied and the patterned structure 40E is bonded to a lid (not shown) or another patterned structure 40E. In these examples, the protective coating 20 would be removed with water prior to grafting. The water and grafting reagents may be introduced using a flow through process.

Figure 6A:
FIG. 6A through FIG. 6G are schematic views that illustrate an example method to apply a protective coating to active areas of a substrate and generate a bonding region that is free of the protective coating.
Figure 6B:
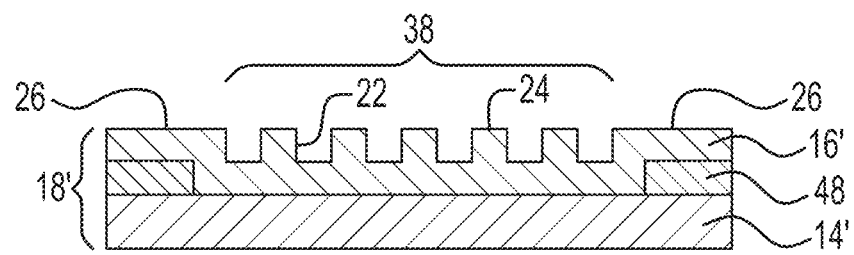

FIG. 6A through FIG. 6G illustrate yet another example of the method. As shown in FIG. 6B, the substrate (which may be a patterned or non-patterned structure as defined herein) is an example of the multi-layer structure 18', which includes a transparent base support 14', a patterned mask layer 48 over the transparent base support 14', and a patterned transparent layer 16' over the patterned mask layer 48 and the transparent base support 14'. In this example, transparent base support 14' and the patterned transparent layer 16' are transparent to ultraviolet wavelengths used in backside ultraviolet light exposure. For example, the transparent base support 14' may be glass and the transparent layer 16 may be tantalum pentoxide or a UV transparent resin. Also, in this example, the patterned mask layer 48 is selected to block at least 75% of the ultraviolet wavelengths that is transmitted through the transparent base support 14' during backside exposure. In an example, patterned mask layer 48 may comprise any ultraviolet opaque or non-transparent metal or ultraviolet opaque semi-metal, such as titanium, chromium, platinum, aluminum, copper, silicon, etc. In one example, the patterned mask layer 48 comprises chromium.

Referring now to FIG. 6A, the patterned mask layer 48 is defined on the transparent base support 14'. In this example, the pattern of the patterned mask layer 48 corresponds with the bonding region 26 for this example of the patterned structure 40 (see FIG. 6C). When a non-patterned structure is used, the patterned mask layer 38 still corresponds with the bonding region 26. A selective deposition technique (e.g., masking and coating) may be used that deposits the patterned mask layer 48 in the desired pattern of the bonding region 26.

As shown in FIG. 6B, the transparent layer 16' may then be deposited over the patterned mask layer 38 and the transparent base support 14' using any suitable deposition technique. The deposited transparent layer 16' may then be patterned to define the patterned region 38, which includes the depressions 22 separated by the interstitial regions 24. The patterning technique used will depend upon the material of the transparent layer 16'. Suitable patterning techniques may include photolithography, nanoimprint lithography (NIL), stamping techniques, embossing techniques, molding techniques, microetching techniques, etc.

As one example, when the transparent layer 16' is a resin, any suitable imprinting technique may be used to generate the patterned region 38. In one example, a working stamp is pressed into the resin while it is soft, which creates an imprint of the working stamp features in the resin. The resin may then be cured with the working stamp in place. Curing may be accomplished by exposure to actinic radiation, such as visible light radiation or ultraviolet (UV) radiation, when a radiation-curable resin material is used; or by exposure to heat when a thermal-curable resin material is used. Curing may promote polymerization and/or cross-linking. As an example, curing may include multiple stages, including a softbake (e.g., to drive off any liquid carrier that may be used to deposit the resin) and a hardbake. The softbake may take place at a lower temperature, ranging from about 50° C. to about 150° C. The duration of the hardbake may last from about 5 seconds to about 10 minutes at a temperature ranging from about 100° C. to about 300° C. Examples of devices that can be used for softbaking and/or hardbaking include a hot plate, oven, etc. After curing, the working stamp is released. This creates topographic features, e.g., depressions 22 separated by interstitial regions 24, in the resin.

As another example, when the transparent layer 16' is tantalum pentoxide, the transparent layer 16' may be etched to generate the patterned region 38. Etching may be performed using inductively coupled plasma (ICP) or reactive ion etching (REI).

During the formation of the multi-layer stack 18', the patterned transparent layer 16' may be activated using silanization or plasma ashing to generate surface groups that can react with the polymeric hydrogel 34.

Figure 6C:
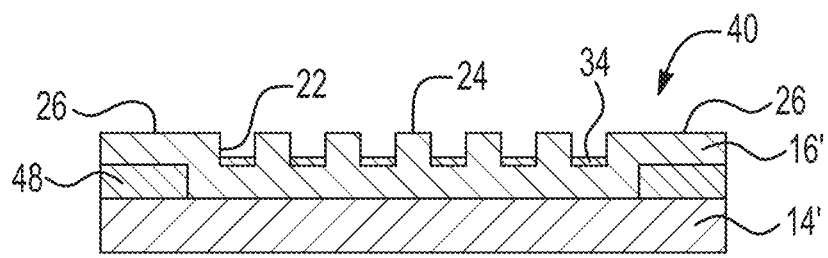

After activation, the polymeric hydrogel 34 may be applied over the transparent layer 16' using any suitable deposition technique. The polymeric hydrogel 34 that is positioned over the interstitial regions 24 and the bonding region 26 may then be removed, e.g., using a polishing process. The patterned structure 40 is shown in FIG. 6C.

Figure 6D:
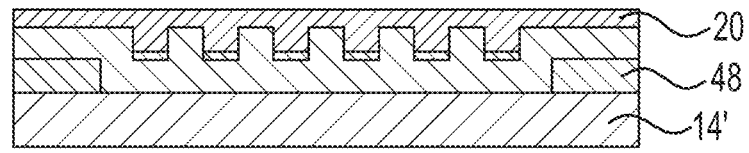
Figure 6E:
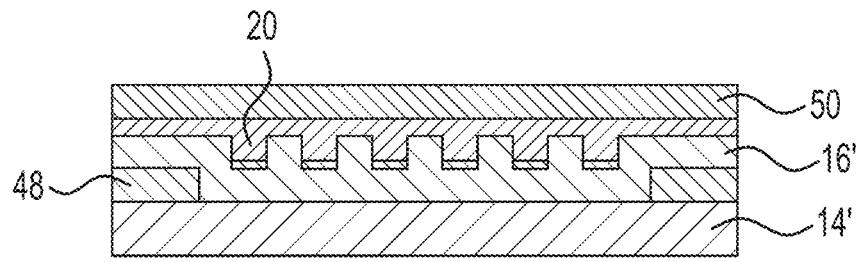

As shown in FIG. 6D, this example method then includes applying and drying the water-soluble protective coating solution to form the protective coating 20 over the patterned region 38 and the bonding region 26. The water-soluble protective coating solution may be applied and dried as described in reference to FIG. 2B.

After drying the water-soluble protective coating solution, this example method further includes applying a negative photoresist 50 over the solid or gel protective coating 20; and exposing the negative photoresist 50 to light through the transparent base support 14', whereby portions of the negative photoresist overlying the patterned region 38 define the insoluble negative photoresist 50', and portions of the negative photoresist 50 overlying the patterned mask layer 48 and the bonding region 26 become soluble. Any example of the negative photoresist set forth herein may be used. Any example of the deposition techniques set forth herein for the negative photoresist may be used.

In this example, it is desirable for the insoluble negative photoresist 50' to remain on the patterned region 38, and to be removed from the bonding region 26. As such, in the example shown in FIG. 6F, the light 52 may be directed through the transparent base support 14'. The negative photoresist 50 on the patterned region 38 will be exposed to the light 52 and will become insoluble. The patterned mask layer 48 (positioned on the bonding region 26) blocks at least 75% of light 52 that is transmitted through the transparent base support 14', thus at least substantially preventing the light 52 from reaching the negative photoresist 50 that is positioned over the bonding region 26. As such, these portions do not become insoluble in the developer, and can be removed with the developer.

Figure 6F:
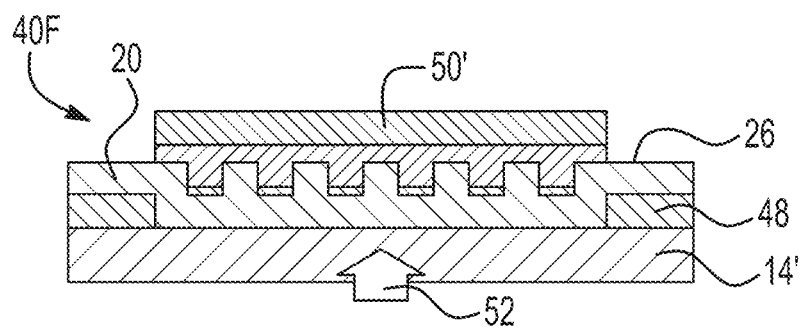

In this example, the selective removal of the portions of the solid or gel protective coating 20 from the bonding region 26 may involve exposing the portions to the developer of the negative photoresist 50. In these examples, the protective coating 20 may be soluble in the developer of the negative photoresist 50. As such, the soluble portions of the negative photoresist 50 and the portions of the protective coating 20 underlying the soluble portions of the negative photoresist 50 may be removed together with the developer. In contrast, the insoluble negative photoresist 50' protects the underlying portions of the protective coating 20 from the developer, and thus these portions of the protective coating 20 remain intact. The resulting patterned structure 40F is shown in FIG. 6F (with the insoluble negative photoresist 50' in place) and FIG. 6G (after insoluble negative photoresist 50' removal).

The insoluble negative photoresist 50' may then be lifted off using a remover. The protective coating 20 is insoluble in the remover, and thus remains at least substantially intact. Suitable removers for the insoluble negative photoresist include dimethylsulfoxide (DMSO), acetone, or an NMP (N-methyl-2-pyrrolidone) based stripper. Any of the removers may be used as long as the protective coating 20 is insoluble in it.

Figure 6G:
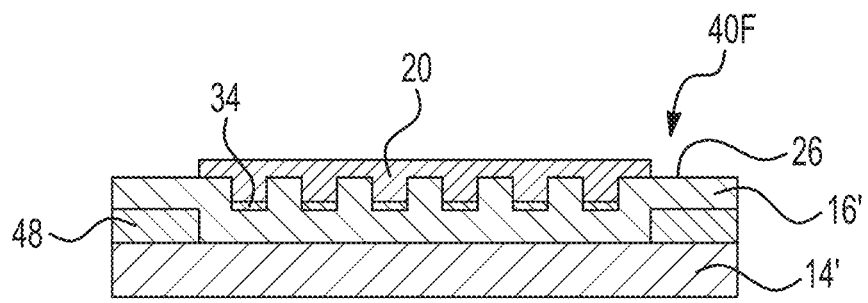

As shown in FIG. 6G, the lift-off process removes at least 95% of the insoluble negative photoresist 50', and thus exposes the underlying protective coating 20. The resulting patterned structure 40F includes the patterned region 38 (and thus the active area 32) being coated with the protective coating 20, while the bonding region 26 is free of the protective coating 20.

The patterned structure 40F may be bonded to another patterned structure 40F or to a lid at the bonding region 26. Any suitable bonding technique, such as laser bonding, diffusion bonding, anodic bonding, eutectic bonding, plasma activation bonding, glass frit bonding, or other methods known in the art may be used to bond two patterned structures 40F or a patterned structure 40F and a lid together. In an example, the spacer layer may be used. The presence of the protective coating 20 may protect any underlying surface chemistry during the bonding process.

If a non-patterned structure is used instead of the patterned structure shown in FIG. 6A through FIG. 6G, the methods would result in the lane 30 (e.g., formed in the transparent substrate 16' in a manner similar to the depressions 22) being coated with the polymeric hydrogel 34 and the protective coating 20, while the bonding region 26 is free of the polymeric hydrogel 34 and the protective coating 20. The non-patterned structures may then be bonded to other non-patterned structures or to a lid at the bonding region 26.

The bond that is formed may be a chemical bond, or a mechanical bond (e.g., using a fastener, etc.).

While not shown in FIG. 6A through FIG. 6G, this method also includes attaching the primer 36A, 36B to the polymeric hydrogel 34. In some examples, the primers 36A, 36B (not shown in FIG. 6A through FIG. 6G) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited and polished, but prior to the application of the protective coating 20 (e.g., at FIG. 6C). In still other examples, the primers 36A, 36B may be grafted after the protective coating 20 is applied and the patterned structure 40F is bonded to a lid (not shown) or another patterned structure 40F. In these examples, the protective coating 20 would be removed with water prior to grafting. The water and grafting reagents may be introduced using a flow through process.

FIG. 7A through FIG. 7E illustrate still another example of the method. This example is performed with the patterned structure, and not with the non-patterned structure. In this example, prior to applying the water-soluble protective coating solution, the method further includes forming the patterned structure by applying a metal layer 42 over a substrate; applying a photoresist 46 over the metal layer 42; patterning the photoresist 46 to generate an insoluble photoresist 46' that defines a depression pattern; etching portions of the metal layer 42 and underlying portions of the substrate according to the depression pattern to form the depressions 22 in the substrate; removing the insoluble photoresist 46'; and applying the polymeric hydrogel 34 in the depressions 22 and over remaining portions of the metal layer 42. Each of these processes will now be described.

Figure 7A:
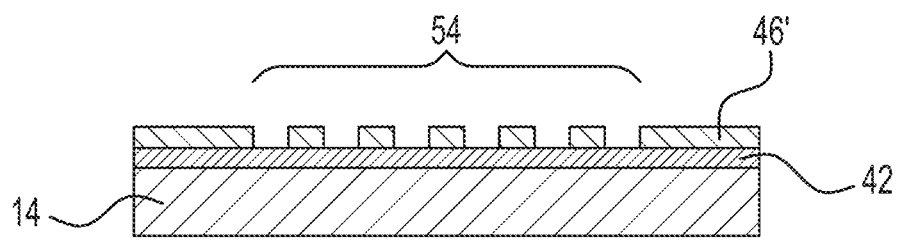
FIG. 7A through FIG. 7E are schematic views that illustrate an example method to apply a protective coating to active areas of a substrate and generate a bonding region that is free of the protective coating.

In FIG. 7A, the substrate is the single layer base support 14. In this example, the single layer base support 14 is not patterned.

In this example method, the metal layer 42 may be applied to the single base support 14. Examples of suitable metals for the metal layer 42 include aluminum, copper, gold, etc. In some examples, the metal may be at least substantially pure (<99% pure). The metal layer 42 may be deposited using any suitable deposition technique.

In this example method, the photoresist 46 may be applied to the metal layer 42. The photoresist 46 may be a negative photoresist or a positive photoresist. In this example, the negative or positive photoresist may be applied and developed to generate a depression pattern 54, as shown in FIG. 7A. From a top view, the depression pattern 54 defines the X-Y location for each depression 22 and interstitial region 24 that is to be formed across the substrate, and also defines the diameter or length and width for each depression 22 that is to be formed across the substrate. In this example, the portions of the photoresist 46 that overly desired bonding region(s) 26 and desired interstitial regions 24 are developed to form the insoluble photoresist 46'. Also in this example, the portions of the photoresist 46 that overly desired depressions 22 are developed to be soluble in the developer. A photomask may be used to direct the light (e.g., ultraviolet light) to the appropriate portions, depending upon the type of photoresist 46 that is used. When the negative photoresist is used, the light is directed toward the desired bonding region(s) 26 and desired interstitial regions 24 to generate the insoluble photoresist 46' and is blocked from the desired depression resions to generate the soluble photoresist. When the positive photoresist is used, the light is directed toward the desired depression regions to generate the soluble photoresist and is blocked from the desired bonding region(s) 26 and desired interstitial regions 24 to generate the insoluble photoresist 46'.

After light exposure, the portion of the photoresist 46 that is soluble in the developer is exposed to the developer, and thus removed. Any of the example developers disclosed herein may be used, depending upon the photoresist 46 that is used. FIG. 7A depicts the insoluble photoresist 46' defining the depression pattern 54.

Figure 7B:
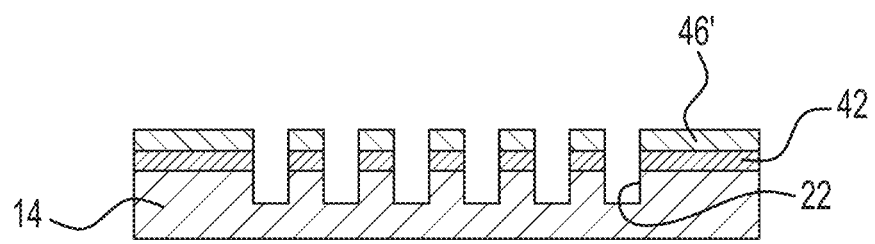

The method then involves etching portions of the metal layer 42 and underlying portions of the single layer base support 14 according to the depression pattern 54 to form the depressions 22 in the single layer base support 14. The etching that is performed will depend upon the material used for the metal layer 42 and the single layer base support 14. As one example, reaction ion etching may be performed with $BCl_3+Cl_2$ to remove portions of an aluminum metal layer 42, and with $SF_6$ and SF6/Ar plasmas to remove portions of a borosilicate glass base support 14. As another example, dry etching may be performed with a narrow gap hydrogen plasma to remove portions of a copper metal layer 42, and with $C_4F_8$ to remove portions of a fused silica base support 14. As shown in FIG. 7B, etching is performed through the thickness of the metal layer 42, and through a portion of the thickness of the base support 14.

The method then involves removing the insoluble photoresist 46'. The insoluble photoresist 46' may be lifted off using any suitable remover. The metal layer 42 and the depressions 22 in the base support 14 are left at least substantially intact when exposed to the remover.

Figure 7C:
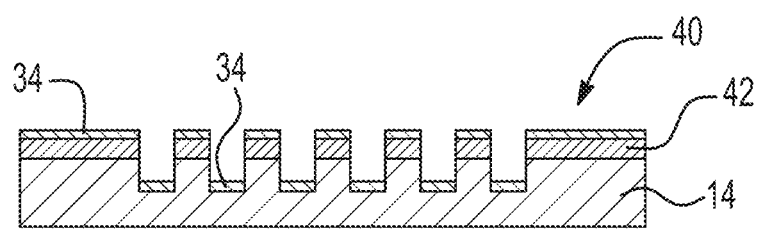

Before or after the insoluble photoresist 46' is removed, the depressions 22 may be activated using silanization or plasma ashing to generate surface groups that can react with the polymeric hydrogel 34. After activation, the polymeric hydrogel 34 may be applied in the depressions 22 and over remaining portions of the metal layer 42. The removal of the insoluble photoresist 46' and the application of the polymeric hydrogel 34 generate the patterned structure 40, as shown in FIG. 7C.

Figure 7D:
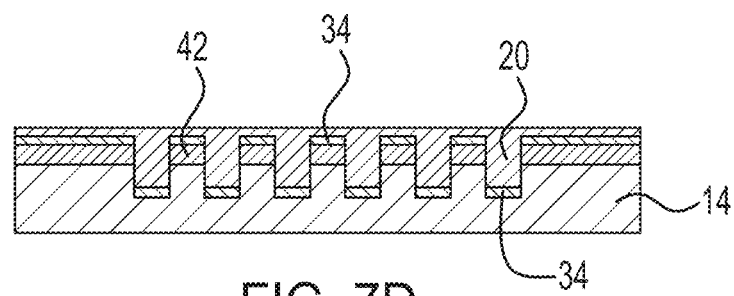

This example method then involves applying and drying the water-soluble protective coating solution to form the protective coating 20 over the patterned region 38 and the bonding region 26. As shown in FIG. 7D, the water-soluble protective coating solution is applied over the polymeric hydrogel 34, both in the depressions 22 and on the interstitial regions 24 and bonding region(s) 26. In these examples, the protective coating 20 is at least 95% soluble in water and is also at least 95% insoluble in a metal remover that is to be used to remove the remaining metal layer 42. The water-soluble protective coating solution may be applied and dried as described in reference to FIG. 2B. FIG. 7D illustrates the resulting protective coating 20.

Figure 7E:
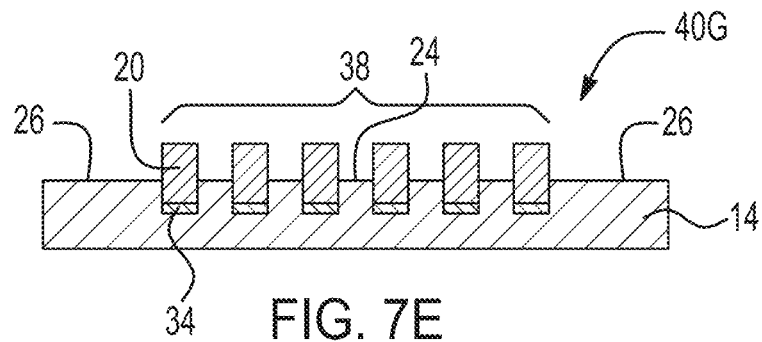

In this example method, selectively removing the portions of the solid or gel protective coating 20 from the bonding region 26 involves lifting off the metal layer 42 using a remover, wherein the protective coating 20 is insoluble in the remover. As examples, an aluminum metal layer may be lifted off using a base solution (e.g., potassium hydroxide (KOH), sodium hydroxide (NaOH), or tetramethylammonium hydroxide (TMAH)), a copper metal layer may be lifted off using $FeCl_3$, and a gold metal layer may be lifted off using a combination of iodine and potassium iodide. As shown in FIG. 7E, the lift-off process removes i) at least 95% of the metal layer 42, ii) polymeric hydrogel 34 thereon, and iii) the protective coating 20 thereon. The other portion of the protective coating 20 (that does not overly the metal layer 42) remains intact over the patterned region 38 because it is insoluble in the remover. The resulting patterned structure 40G includes the patterned region 38 (and thus the active area 32) being coated with the protective coating 20, while the bonding region 26 is free of the protective coating 20. In this example, the interstitial regions 24 are also free of the protective coating 20.

The patterned structure 40G may be bonded to another patterned structure 40G or to a lid at the bonding region 26. Any suitable bonding technique, such as laser bonding, diffusion bonding, anodic bonding, eutectic bonding, plasma activation bonding, glass frit bonding, or other methods known in the art may be used to bond two patterned structures 40G or a patterned structure 40G and a lid together. In an example, the spacer layer may be used. The presence of the protective coating 20 may protect any underlying surface chemistry during the bonding process.

While not shown in FIG. 7A through FIG. 7E, this method also includes attaching the primer 36A, 36B to the polymeric hydrogel 34. In some examples, the primers 36A, 36B (not shown in FIG. 7A through FIG. 7E) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited and polished, but prior to the application of the protective coating 20 (e.g., at FIG. 7C). In still other examples, the primers 36A, 36B may be grafted after the protective coating 20 is applied and the patterned structure 40G is bonded to a lid (not shown) or another patterned structure 40G. In these examples, the protective coating 20 would be removed with water prior to grafting. The water and grafting reagents may be introduced using a flow through process.

Figure 8A:
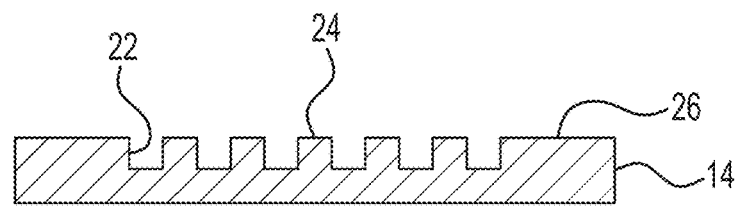
FIG. 8A through FIG. 8C are schematic views that illustrate an example method to apply a protective coating to active areas of a substrate and generate a bonding region that is free of the protective coating.
Figure 8B:
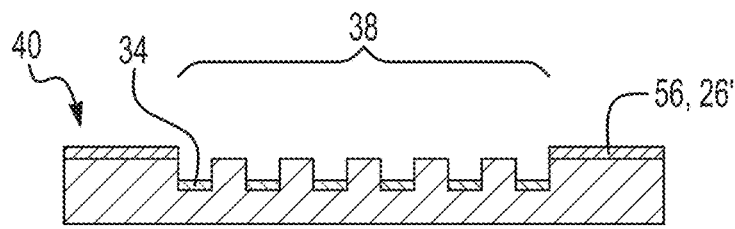
Figure 8C:
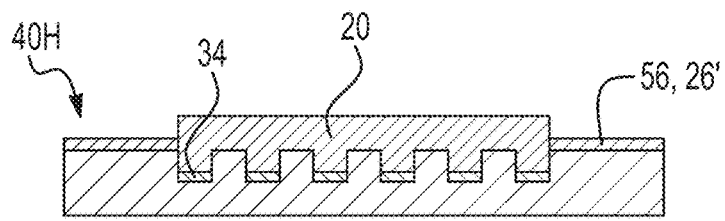

Still another example method is depicted in FIG. 8A through FIG. 8C. As shown in FIG. 8A, the substrate is the single layer base support 14 with the depressions 22 defined in one surface of the single layer base support 14. The depressions 22 may be defined via etching, imprinting, lithography, or another suitable technique. While the single layer base support 14 is depicted, it is to be understood that these example methods may be performed with a multi-layer structure 18, where the depressions 22 are defined in the outermost layer 16 (see FIG. 1B).

In this example method, prior to applying the polymeric hydrogel 34 or the water-soluble protective coating solution, the method includes applying a hydrophobic layer 56 over the bonding region 26 to form a hydrophobic bonding region 26'. This is shown in FIG. 8B. Examples of the hydrophobic layer 56 may be selected from the group consisting of a fluorinated polymer, a perfluorinated polymer, a silicon polymer, and a mixture thereof. As specific examples, the hydrophobic layer 56 may include an amorphous fluoropolymer (commercially available examples of which include those in the CYTOP® series from AGC Chemicals, which have one of the following terminal functional groups: A type: —COOH, M type: —CONH—Si(OR)$_n$, or S type: —CF$_3$), a polytetrafluoroethylene (a commercially available example of which is TEFLON® from Chemours), parylen, a fluorinated hydrocarbon, a fluoroacrylic copolymer (a commercially available example of which includes as FLUOROPEL® from Cytonix).

The hydrophobic layer 56 may be deposited over the bonding region 26 using any suitable selective deposition technique. Some specific examples include screen printing, inkjet printing, microcontact printing, or spray coating through a mask. In other examples, a photoresist 46 (not shown in FIG. 8A through FIG. 8C) may be developed across the entire base support 14 and then dry etched to expose the bonding region 26. In these examples, the insoluble photoresist 46' (also not shown in FIG. 8A through FIG. 8C) may remain in place over the depressions 22 and interstitial regions 24 during hydrophobic layer 56 deposition, and may be removed after the hydrophobic bonding region 26' is formed. In still other examples, the hydrophobic layer 56 may be deposited across the entire base support 14, and then portions may be exposed to laser irradiation to remove the hydrophobic layer 56 from the depressions 22 and interstitial regions 24.

Once the hydrophobic bonding region 26' is formed, the exposed portions of the base support 14 or of the outermost layer 16 of the multi-layer structure 18 may be activated using silanization or plasma ashing to generate surface groups that can react with the polymeric hydrogel 34. After activation, the polymeric hydrogel 34 may be applied over the base support 14 or the outermost layer 16 of the multi-layer structure 18 using any suitable deposition technique. The polymeric hydrogel 34 is repelled by the hydrophobic bonding region 26', and thus does not apply to this region 26'. As such, the polymeric hydrogel 34 is positioned in the depressions 22 and over the interstitial regions 24. The polymeric hydrogel 34 over the interstitial regions 24 may then be removed, e.g., using a polishing process. The hydrophobic bonding region 26' remains at least substantially intact after polishing. The resulting patterned structure 40 is shown in FIG. 8B.

The method then includes applying the water-soluble protective coating solution over the patterned region 38 of the patterned structure 40. Any example of water-soluble protective coating solution disclosed herein may be used in this example. The water-soluble protective coating solution may be applied using dip coating, dunk coating, spin coating, spray coating, ultrasonic spray coating, doctor blade coating, aerosol printing, or inkjet printing.

In this example, the water-soluble protective coating solution is repelled by the hydrophobic bonding region 26'. Thus, the hydrophobic bonding region 26' of the patterned structure remains exposed after the water-soluble protective coating solution is applied over the patterned region 38. The water-soluble protective coating solution is then dried as described herein to form the protective coating 20 over the patterned region 38, but not over the hydrophobic bonding region 26'. FIG. 8C illustrates the resulting protective coating 20 and the patterned structure 40H.

The patterned structure 40H may be bonded to another patterned structure 40H or to a lid at the hydrophobic bonding region 26'. Any suitable bonding technique, such as laser bonding, diffusion bonding, anodic bonding, eutectic bonding, plasma activation bonding, glass frit bonding, or other methods known in the art may be used to bond two patterned structures 40H or a patterned structure 40H and a lid together. In an example, the spacer layer may be used. The presence of the protective coating 20 may protect any underlying surface chemistry during the bonding process.

If a non-patterned structure is used instead of the patterned structure shown in FIG. 8A through FIG. 8C, the methods would result in the lane 30 being coated with the polymeric hydrogel 34 and the protective coating 20, and the bonding region 26 being coated with the hydrophobic layer 56 but not with the polymeric hydrogel 34 or the protective coating 20. The non-patterned structures may then be bonded to other non-patterned structures or to a lid at the hydrophobic bonding region 26'. The bond that is formed may be a chemical bond, or a mechanical bond (e.g., using a fastener, etc.).

While not shown in FIG. 8A through FIG. 8C, this method also includes attaching the primer 36A, 36B to the polymeric hydrogel 34. In some examples, the primers 36A, 36B (not shown in FIG. 8A through FIG. 8C) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited and polished, but prior to the application of the protective coating 20 (e.g., at FIG. 8B). In still other examples, the primers 36A, 36B may be grafted after the protective coating 20 is applied and the patterned structure 40H is bonded to a lid (not shown) or another patterned structure 40H. In these examples, the protective coating 20 would be removed with water prior to grafting. The water and grafting reagents may be introduced using a flow through process.

Figure 9A:
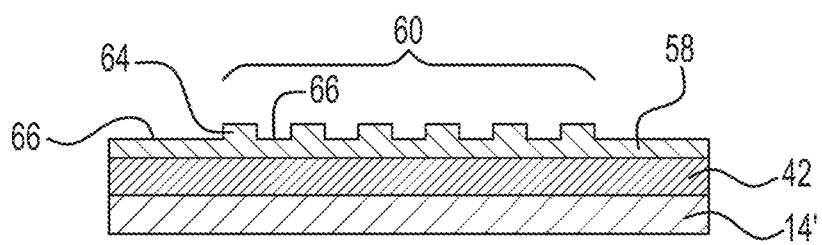
FIG. 9A through FIG. 9I are schematic views that illustrate an example method to apply a protective coating to active areas of a substrate and generate a bonding region that is free of the protective coating.
Figure 9B:
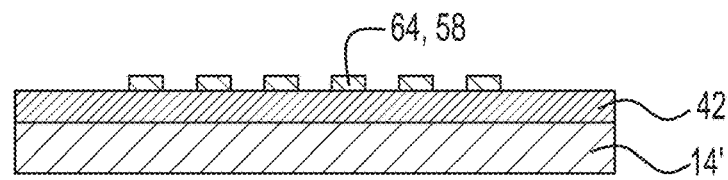
Figure 9C:
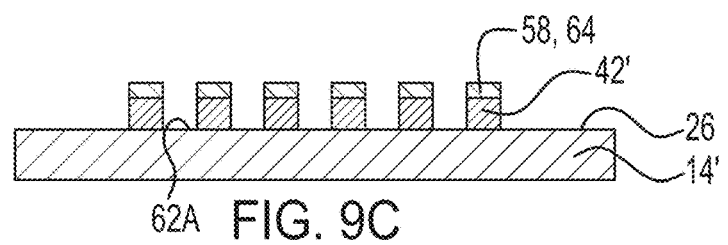
Figure 9D:
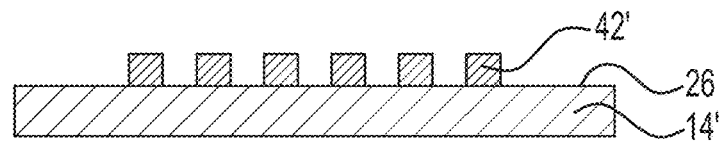
Figure 9E:
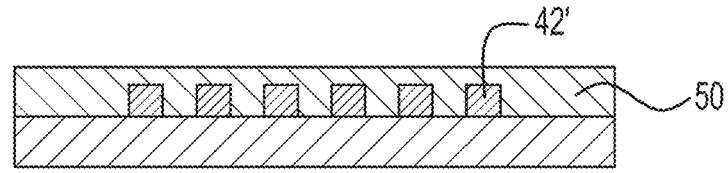
Figure 9F:
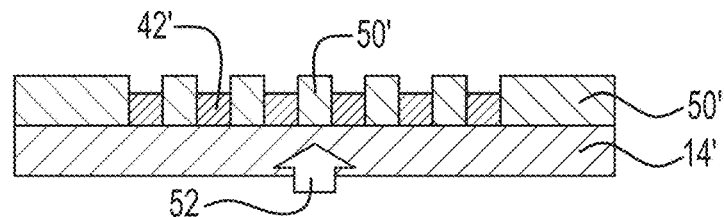
Figure 9G:
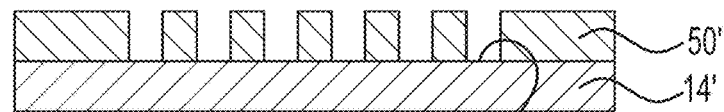
Figure 9H:
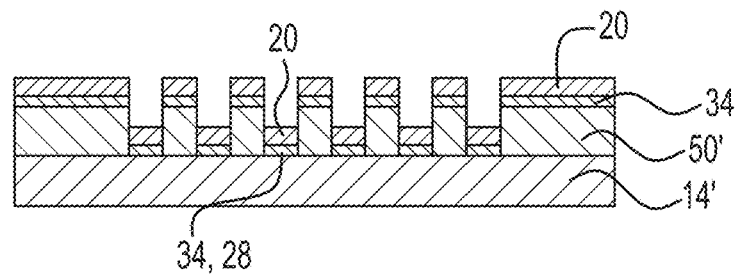
Figure 9I:
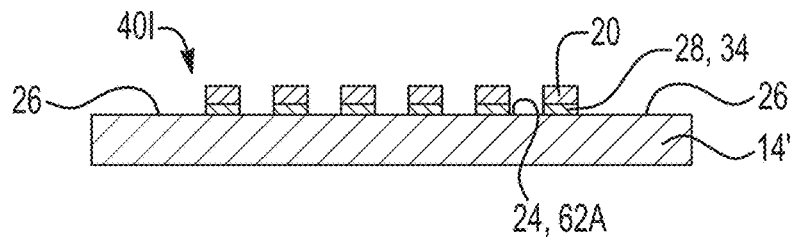

FIG. 9A through FIG. 9I illustrate still another example of the method. This example method generates a plurality of functionalized pads 28 on the substrate surface (see FIG. 9I). This method generally involves patterning a metal layer 42 on a transparent base support 14' to define i) metal posts 42' separated by first interstitial regions 62A of the transparent base support 14', and ii) a bonding region 26 of the transparent base support 14' (FIG. 9C); generating an insoluble negative photoresist 50' over the first interstitial regions 62A and the bonding region 26 (FIG. 9F); etching the metal posts 42' to expose second interstitial regions 62B of the transparent base support 14' (FIG. 9G); applying the polymeric hydrogel 34 over the insoluble photoresist 50' and the second interstitial regions 62B (FIG. 9H); applying the water-soluble protective coating solution over the polymeric hydrogel 34 (FIG. 9H); drying the water-soluble protective coating solution to form a solid coating or a gel coating (protective coating 20) over the polymeric hydrogel 34; and lifting off the insoluble negative photoresist 50' to expose coated functionalized pads 28, the bonding region 26, and the first interstitial regions 62A (which are interstitial regions 24) (FIG. 9I). Each of these processes will now be described.

In FIG. 9A, the substrate is the transparent base support 14'. In this example, the transparent base support 14' is not patterned and is transparent to ultraviolet wavelengths used in backside ultraviolet light exposure. As one example, the transparent base support 14' may be glass.

In this example method, the metal layer 42 may be applied to the transparent base support 14'. Examples of suitable metals for the metal layer 42 include aluminum, copper, gold, etc. In some examples, the metal may be at least substantially pure (<99% pure). The metal layer 42 may be deposited using any suitable deposition technique.

In this example method, a resin layer 58 may be applied over the metal layer 42. The resin layer 58 may be any resin that can be patterned, e.g., via nanoim print lithography, with a pad pattern 60. From a top view, the pad pattern 60 defines the X-Y location for each functionalized pad 28 and interstitial region 24 that is to be formed across the substrate, and also defines the diameter or length and width for each functionalized pad 28 that is to be formed across the substrate.

As shown in FIG. 9A, the resin layer 58 is imprinted to form the pad pattern 60. The pad pattern 60 includes convex regions 64 that correspond with the areas where the functionalized pads 28 will be formed, and lower regions 66 (relative to the convex regions 64) that correspond with the areas where the interstitial regions 24 and bonding region 26 will be formed. Any suitable imprinting technique may be used. In one example, a working stamp is pressed into the resin layer 58 while it is soft, which creates an imprint of the working stamp features in the resin layer 58. The resin layer 50 may then be cured with the working stamp in place. After curing, the working stamp is released. In this example method, the working stamp does not extend through the entire depth of the resin layer 58, and thus the underlying metal layer 42 is not exposed after imprinting (as shown in FIG. 9A).

The resin layer 58 is then selectively etched to expose portions of the metal layer 42. This is shown in FIG. 9B. Any exposed areas of the resin layer 58 may be etched during this process. As the lower regions 66 of the resin layer 58 are thinner than the convex regions 64, the resin layer 58 at the lower regions 66 will be etched away. Etching may be continued until metal layer 42 underlying the lower regions 66 is exposed, and resin layer 58 at the convex regions 64 remain. The metal layer 42 (underlying the lower regions 66) may act as an etch stop. Etching of the resin layer 58 may involve a dry etching process, such as an anisotropic oxygen plasma or a mixture of 90% $CF_4$ and 10% $O_2$ plasma.

The metal layer 42 is then patterned using the remaining convex regions 64 of the resin layer 58. A metal dry etching process may be used to etch away the metal that is not covered by the convex regions 64 of the resin layer 58. In one example, the metal layer 42 may be etched using a chlorine-based plasma (e.g., $BCl_3+Cl_2$). The transparent based support 14' may act as an etch stop. This etching process results in the formation of the metal posts 42', which are separated by first interstitial regions 62A of the transparent base support 14', as shown in FIG. 9C. This process also defines the bonding region 26.

The convex regions 64 of the resin layer 58 may then be selectively etched to expose the metal posts 42'. Etching may be continued until the convex regions 64 are removed and the metal posts 42' are exposed. This is shown in FIG. 9D. The metal posts 42' may act as an etch stop. Etching of the convex regions 64 may involve a dry etching process, such as an anisotropic oxygen plasma or a mixture of 90% $CF_4$ and 10% $O_2$ plasma. This etching process may also not affect the exposed portions of the transparent base support 14'.

As shown in FIG. 9E and FIG. 9F, this method also involves generating an insoluble negative photoresist 50' over the first interstitial regions 62A and the bonding region 26. In an example, generating the insoluble negative photoresist 50' involves applying a negative photoresist 50 over the metal posts 42', the first interstitial regions 62A, and the bonding region 26 (as shown in FIG. 9E); exposing the negative photoresist 50 to light 52 through the transparent base support 14', whereby portions of the negative photoresist 50 overlying the first interstitial regions 62A and the bonding region 26 define the insoluble negative photoresist 50', and portions of the negative photoresist 50 overlying the metal posts 42' become soluble (as shown in FIG. 9F); and removing the soluble portions of the negative photoresist 50 (as shown in FIG. 9F).

Any example of the negative photoresist 50 set forth herein may be used. Any example of the deposition techniques set forth herein for the negative photoresist 50 may be used.

In this example, it is desirable for the insoluble negative photoresist 50' to remain on the first interstitial regions 62A and the bonding region 26, and to be removed from the metal posts 42'. As such, in the example shown in FIG. 9F, the light 52 may be directed through the transparent base support 14'. The negative photoresist 50 on the transparent base support 14' will be exposed to the light 52 and will become insoluble. The metal posts 42' block at least 75% of light 52 that is transmitted through the transparent base support 14', thus at least substantially preventing the light 52 from reaching the negative photoresist 50 that is positioned over the metal posts 42'. As such, these portions do not become insoluble in the developer, and can be removed with the developer.

The metal posts 42' may then be removed with a wet etch process. As examples, aluminum metal posts 42' can be removed in acidic or basic conditions, copper metal posts 42' can be removed using $FeCl_3$, copper, gold or silver metal posts 42' can be removed in an iodine and iodide solution, and titanium metal posts 42' can be removed using $H_2O_2$. In these examples, the transparent base support 14' acts as an etch stop for the metal post etching process. The removal of the metal posts 42' exposes the second interstitial regions 62B of the transparent base support 14'. As shown in FIG. 9G, the insoluble negative photoresist 50' remains at least substantially intact when the metal posts 42' are removed.

The second interstitial regions 62B may then be activated using silanization or plasma ashing to generate surface groups that can react with the polymeric hydrogel 34. After activation, the polymeric hydrogel 34 may be applied over the second interstitial regions 62B and over the insoluble negative photoresist 50'. The polymeric hydrogel 34 applied over the second interstitial regions 62B forms the functionalized pads 28. This is shown in FIG. 9H.

This example method then involves applying and drying the water-soluble protective coating solution to form the protective coating 20 over the polymeric hydrogel 34. This is also shown in FIG. 9H. As shown in FIG. 9H, the water-soluble protective coating solution is applied over the polymeric hydrogel 34, and thus is also over the second interstitial regions 62B and over the insoluble negative photoresist 50'. In these examples, the protective coating 20 is at least 95% soluble in water and is also at least 95% insoluble in a remover that is to be used to remove the insoluble negative photoresist 50'. The water-soluble protective coating solution may be applied and dried as described in reference to FIG. 2B.

The insoluble negative photoresist 50' may then be lifted off to expose functionalized pads 28 that are coated with the protective coating 20, the bonding region 26, and the first interstitial regions 62A (which are interstitial regions 24). The insoluble negative photoresist 50' may then be lifted off using a remover. Suitable removers for the insoluble negative photoresist 50' include dimethylsulfoxide (DMSO), acetone, or an NMP (N-methyl-2-pyrrolidone) based stripper. Any of the removers may be used as long as the protective coating 20 is insoluble in it.

As shown in FIG. 9I, the lift-off process removes at least 95% of the insoluble negative photoresist 50', and the portions of the polymeric hydrogel 34 and protective coating 20 that overlie the insoluble negative photoresist 50'. The protective coating 20 is insoluble in the remover, and thus the portions of the protective coating 20 that overlie the functionalized pads 28 remain at least substantially intact. The resulting patterned structure 40I includes the functionalized pads 28 (the active areas in this example) being coated with the protective coating 20, while the bonding region 26 is free of the protective coating 20.

The patterned structure 40I may be bonded to another patterned structure 40I or to a lid at the bonding region 26. Any suitable bonding technique, such as laser bonding, diffusion bonding, anodic bonding, eutectic bonding, plasma activation bonding, glass frit bonding, or other methods known in the art may be used to bond two patterned structures 40I or a patterned structure 40I and a lid together. In an example, the spacer layer may be used. The presence of the protective coating 20 may protect any underlying surface chemistry during the bonding process.

While not shown in FIG. 9A through FIG. 9I, this method also includes attaching the primer 36A, 36B to the polymeric hydrogel 34. In some examples, the primers 36A, 36B (not shown in FIG. 9A through FIG. 9I) may be pre-grafted to the polymeric hydrogel 34 and thus will be applied to the substrate when the polymeric hydrogel 34 is applied. In other examples, the primers 36A, 36B may be grafted after the polymeric hydrogel 34 is deposited, but prior to the application of the protective coating 20 (e.g., at FIG. 9H). In still other examples, the primers 36A, 36B may be grafted after the protective coating 20 is applied and the patterned structure 40I is bonded to a lid (not shown) or another patterned structure 40I.

In this example, the patterned structure 40I (and thus a flow cell 10 including the patterned structure 40I) includes a substrate (e.g., 14 or 18), a plurality of functionalized pads 28 on the substrate and isolated from each other by interstitial regions 24, where each of the plurality of functionalized pads 28 includes a polymeric hydrogel 34 and primers 36A, 36B attached to the polymeric hydrogel 34, and a protective coating 20 over the plurality of functionalized pads 28 and not over the interstitial regions 24.

Throughout the methods shown and described in reference to the FIG. 2 series through the FIG. 9 series, it is to be understood that the water-soluble protective coating solution is applied to generate the coating 20. It is to be understood, however, that the water-soluble protective coating solution may also be applied with other coating solutions, including with the polymeric hydrogel 34, polishing solutions, grafting solutions, wash buffers, etc. This should effectively prevent any dry-staging related polymeric hydrogel 34 degradation.

Protective Coating and Other Active Material Deposition Methods

Other examples of the method disclosed herein may be used to selectively apply the protective coating 20 or other active area materials, such as the polymeric hydrogel 34 (with or without primers 36A, 36B grafted thereto) with high precision. As an example, the material may be dispensed in lines having a width ranging from about 300 µm to about 1 mm. The precision of the dispensed lines renders this method particularly desirable for dispensing the polymeric hydrogel 34 (with or without primers 36A, 36B grafted thereto) or the water-soluble protective coating solution in the lanes 30 of a substrate. These lanes 30 may be patterned with depression 22 or functionalized pads 28, or they may be non-patterned. As another example, the material may be dispensed as dots having a diameter ranging from about 0.5 mm to about 2 mm. The precision of the dispensed dots renders this method particularly desirable for dispensing the water-soluble protective coating solution on fiducials, or dispensing the polymeric hydrogel 34 (with or without primers 36A, 36B grafted thereto) and/or the water-soluble protective coating solution in larger depressions 22, or dispensing the polymeric hydrogel 34 (with or without primers 36A, 36B grafted thereto) to form larger functionalized pads 28, or dispensing the water-soluble protective coating solution on larger functionalized pads 28. The material may also be dispensed in the shape of arcs. Combinations of lines, dots and/or arcs may also be used to generate hierarchal shapes.

During this example method, the bonding region 26 remains free of the active area materials and/or the protective coating 20, and thus the method may reduce material waste. Additionally, it may be desirable to keep the protective coating 20 from depositing on the bonding region 26 as it may interfere with achieving an effective bond.

Figure 10:
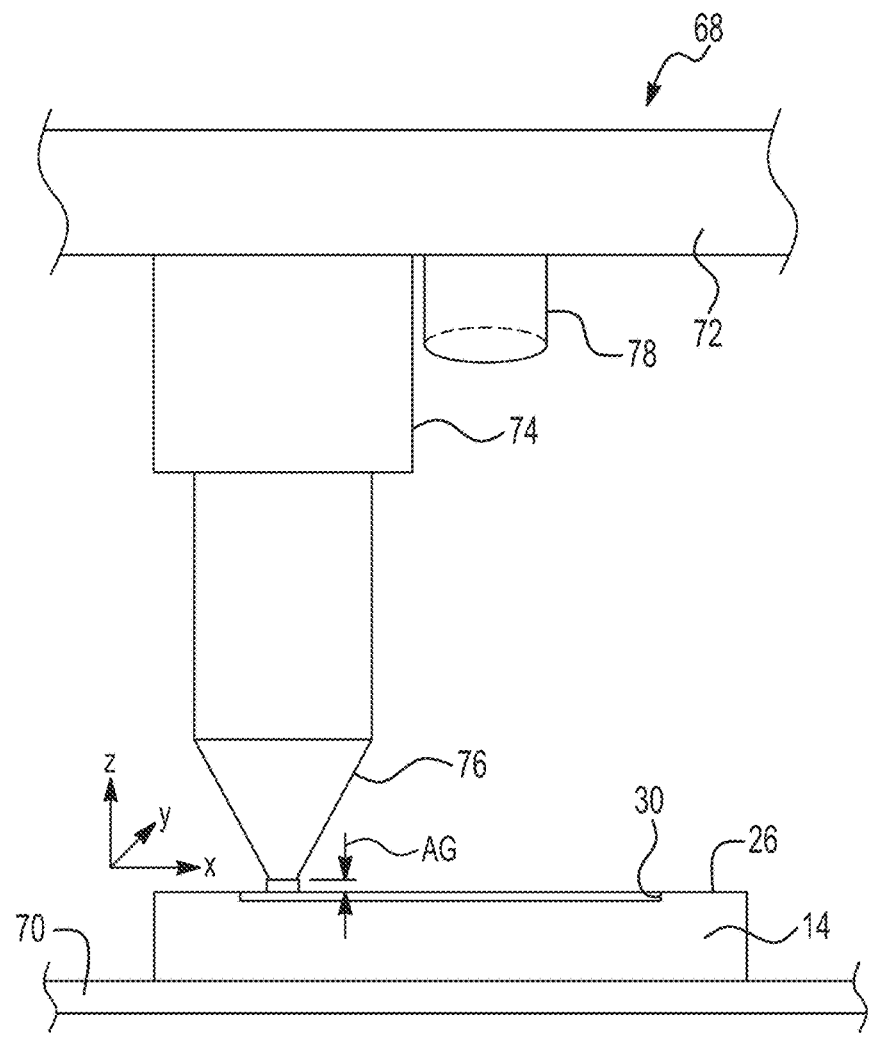
FIG. 10 is a schematic illustration of a precision gantry tool used in another example of a method disclosed herein.

The tool used in this example method is a precision gantry tool 68, which is shown schematically in FIG. 10. While not shown, it is to be understood that the precision gantry tool 68 includes a controller that is to control the components of the tool 68 in response to user input or pre-programmed instructions.

The tool 68 may include a carrier tray 70 to support the single layer base support 14 or the multi-layer structure 18 having a feature (e.g., a lane 30, depressions 22, a fiducial, etc.) defined therein or defined thereon. As described herein, the feature may be imprinted, etched, or otherwise fabricated in the support 14 or structure 18 at the outermost surface. Alternatively, the feature may be defined by another material (e.g., one or more spacer layers) that is positioned on the outermost surface of an at least substantially flat single layer base support 14 or multi-layer structure 18.

The precision gantry tool 68 also includes the gantry 72 which is moveable in the X and Y directions with respect to the XY plane of the carrier tray 70. The gantry 72 can move any components attached thereto in the X and Y directions.

Attached to the gantry 72 is a pump 74 with a nozzle 76 that can dispense volumes of fluid, such as a mixture including the polymeric hydrogel 34 (pre-grafted or not) and/or the water-soluble protective coating solution, at a precise volumetric flow rate. The volumetric flow rate may range from about 0.15 µL/s to about 20 µL/s. In one example, the volumetric flow rate may be 2 µL/s. In another example, the volumetric flow rate ranges from about 0.16 µL/s to about 5 µL/s.

Any suitable pump 74 and nozzle 76 may be used.

In one example, the pump 74 is a progressive cavity pump. Some pumps, such as pressure based pumps, may be less desirable as they lack a dispense rate and they enable little or no control over the thickness of the dispensed material. These pumps can lead to uncontrolled reflow (undesirable spreading) in the X and Y directions, which does not allow for precise dispensing. The progressive cavity pump helps to keep the thickness of the dispensed material at or below 10 µm. In some examples, the depth of the flow channel 12 between two patterned or non-patterned structures may range from about 75 µm to about 100 µm. In these examples, the progressive cavity pump may be used to generate multiple layers of dispensed material on each of the structures so that the total thickness on the respective structures ranges from less than 37.5 µm to less than 50 µm (so that the dispensed materials do not completely fill the flow channel 12).

In one example, the nozzle 76 is a metal nozzle. Metal nozzles may be particularly desirable, in part because metal nozzles are less susceptible than plastic nozzles to pressure build up, and nozzle expansion as a result of the pressure build up. Nozzle expansion can alter the air gap AG, which can deleteriously affect the meniscus of the material being dispensed, which can lead to undesirable spreading. The shape of the nozzle 76 can also help reduce pressure buildup issues. For example, conical nozzles are less susceptible than cylindrical nozzles to pressure build up. Metal nozzles coated, on the interior and/or on the exterior, with a hydrophobic layer may also be desirable to help prevent clogging. Any suitable hydrophobic material may be used as the coating. Some hydrophobically coated metal nozzles are commercially available.

One specific example of the nozzle 76 is a stainless steel conical nozzle having a tip diameter of 1 mm or less. The gauge of the nozzle 76 may affect the line fidelity of the dispensed material. In the examples disclosed herein, the nozzle gauge ranges from about 17 to about 30. As examples, the 17 gauge nozzle can produce a 1.2 mm line width and the 30 gauge nozzle can produce a 300 µm line width.

During the method, the nozzle 76 may be moved in the X and/or Y directions by the gantry 72 (which is operated by the controller), and may also be controlled to move in the Z direction by the controller. A height sensor (not shown) may be mounted to the gantry 72 in order to measure the position of the substrate along the vertically-oriented Z axis for determining a proper dispense height. The dispense height corresponds with an air gap AG between the tip of the nozzle 76 and the surface of the substrate, e.g., support 14 or structure 18. Controlling the nozzle 76 position in the Z direction enables a particular air gap AG to be achieved. The present inventors have found that controlling the air gap AG contributes to achieving precisely dispensed materials. For example, if the air gap AG is too big, continuous deposition may not be achieved and the nozzle 76 may produce droplets not in contact with the substrate that spontaneously break off. Uncontrolled spreading may also occur with a large air gap AG, but this is dependent on the flow rate being high enough to maintain a meniscus at the large air gap AG. This is undesirable, as the material can spread, e.g., into an adjacent lane 30, onto the bonding region 26, etc. For precisely dispensing into the lanes 30 having the dimensions disclosed herein, the air gap AG ranges from greater than 0 µm to about 100 µm. In other examples, the air gap AG ranges from about 45 µm to about 85 µm, from about 50 µm to about 70 µm, etc. In one specific example, the air gap AG is about 65 µm.

During the method, the speed of the gantry 72 may be controlled. In an example, linear gantry speed ranges from about 75 mm/s to about 350 mm/s may be used.

Also attached to the gantry 72 is a camera 78. An example of the camera 78 is machine vision camera. The camera 78 may be controlled (e.g., by a controller, not shown) to identify locations on the support 14 or structure 18 where dispensing is desirable. The support 14 or structure 18 may include fiducials to aid in location identification.

An example of the method using the precision gantry tool 68 includes positioning a substrate (e.g., support 14 or structure 18), having a feature (e.g., lane 30) defined therein, with respect to the nozzle 76 of the precision dispense tool 68 such that an air gap AG between a surface of the substrate and a surface of the nozzle 68 ranges from greater than 0 µm to about 100 µm; and dispensing i) an aqueous hydrogel solution (including the polymeric hydrogel 34), ii) a pre-grafted aqueous hydrogel solution (including the pre-grafted polymeric hydrogel 34), or iii) a water-soluble protective coating solution from the nozzle 76 into the feature at a flow rate ranging from about 0.15 µL/s to about 20 µL/s, whereby the surface of the substrate surrounding the feature remains free of i) the aqueous hydrogel solution, ii) the pre-grafted aqueous hydrogel solution, or iii) the water-soluble protective coating solution.

As one example, the feature may be the lane 30 that is non-patterned or that is patterned within depressions 22 or functionalized pads 28, and the surface of the substrate surrounding the feature(s) may be the bonding region 26. As another example, the feature may be a fiducial, and the surface of the substrate surrounding the feature may be interstitial regions around the fiducial. As still another example, the feature may be a depression 22 having a diameter of 150 μm or more, and the surface of the substrate surrounding the feature may be interstitial regions 24 around the depression 22.

To dispense a pattern of fluid onto the substrate (e.g., support 14 or structure 18) held in the carrier tray 70, the controller first determines the location and orientation of the substrate in the horizontally oriented XY plane in which the substrate generally lies. The camera 78 may scan the substrate and capture visual images of reference fiducials provided on the top surface of the substrate by traveling along a path that moves across pre-programmed locations of the reference fiducials which are known by the controller. Using the captured visual images, the controller can determine the actual location and orientation of the substrate and its features in the XY plane. The height sensor measures the position of the substrate along the vertically-oriented Z axis for determining a proper air gap AG. The controller then operates the gantry 72 to move the nozzle 76 along the X and Y axes until the applicator is properly positioned in the XY plane over a desired feature of the substrate positioned below. The nozzle 76 is then lowered along the Z axis until the nozzle tip is positioned at the proper dispensing height with respect to the substrate surface so that the proper air gap AG is obtained. The pump 74 may be operated in conjunction with the gantry 72 in the X, Y, and or Z directions to dispense the desired pattern. The coordination and relative rates of the pump 74 and the gantry 72 contributes to the pattern fidelity of the dispensed coating. Upon completion of dispensing, the nozzle 76 is then raised back up along the Z axis and moved to an end position, a soaking position, or to another feature for additional dispensing.

The dispensed material may be dried, e.g., by warming, heating, evaporation, vacuum exposure, convective drying, or the like.

Any of the fluids disclosed herein may be dispensed using the precision gantry tool 68 and the dispensing parameters set forth herein in order to achieve high precisions lines, arcs, or dots and a reduction of wasted material. In one example, the dispensing is performed to form a layer, in or on the substrate feature, of the i) the aqueous hydrogel solution, ii) the pre-grafted aqueous hydrogel solution, or iii) the water-soluble protective coating solution having a thickness of about 10 μm or less.

This method creates lines, arcs, or dots of the dispensed material with high precision. This method may also be used to combine lines and/or arcs and/or dots to form hierarchal shapes, such as filled in rectangle, circles, or more complex geometries. When used to deposit the water-soluble protective coating solution or the polymeric hydrogel 24 (pre-grafted or not) into the lane 30 that is not patterned within depressions 22 or functionalized pads 28, the deposited solution forms a hierarchal shape of precise lines within the lane 30 that does not extend out onto the surrounding bonding regions 26.

This example method may also involve maintaining the nozzle 76 in water before and after the dispensing. The water may be located in a reservoir, which provides a soaking position for the nozzle 76 between dispensing steps. This may be particularly desirable for maintaining the health of stainless steel conical nozzles, as it helps to prevent clogging. Soaking may also be desirable when dispensing polymer solutions that may dry out in the nozzle 76 and cause clogging when exposed to air.

When the protective coating 20 is dispensed using the precision gantry tool 68, it is to be understood that the polymeric hydrogel 34 may also be applied using the precision gantry tool 68, or may be applied by using other application techniques. For example, the polymeric hydrogel 34 may be deposited in the non-patterned lane 30 using any suitable deposition technique. For another example, the polymeric hydrogel 34 may be deposited in the patterned lane 30 using any suitable deposition technique, followed by polishing to remove the hydrogel 34 from the interstitial regions 24.

To further illustrate the present disclosure, examples are given herein. It is to be understood that these examples are provided for illustrative purposes and are not to be construed as limiting the scope of the present disclosure.

NON-LIMITING WORKING EXAMPLES

Example 1

A method similar to that shown in FIG. 4A through FIG. 4E was used to apply KOLLICOAT® IR (a polyvinyl alcohol/polyethylene glycol graft copolymer available from BASF Corp.) on a non-patterned glass slide having lanes etched therein. This method did not apply any of the active area materials, but rather was performed to demonstrate the effectiveness of the photoresist for selectively applying the protective coating.

First, a negative photoresist (e.g., NR9-1500P, NR9-1500PY, NR9-1000P, NR9-1000PY) was applied to the entire non-patterned glass slide, including in the lanes, and the bonding region surrounding the lanes were exposed to UV light to generate insoluble portions on the bonding regions. The non-patterned glass slide was exposed to a developer (e.g., RD6), which removed the soluble negative photoresist from the lanes.

Next, an aqueous solution including 5 wt % KOLLICOAT® IR and 5 wt % ethanol was spin coated onto the non-patterned glass slide. The aqueous solution coated the lanes and the insoluble negative photoresist on the bonding regions. The aqueous solution was dried at a temperature ranging from about 40° C. to about 60° C. to perform a protective coating.

Finally, the non-patterned glass slide, with the various materials coated thereon, was exposed to acetone with 1 minute of sonication, followed by fresh acetone with 4 minutes of sonication. Acetone was selected because it is a lift-off reagent for the insoluble negative photoresist, and because the protective coating is not soluble in it.

Figure 11:
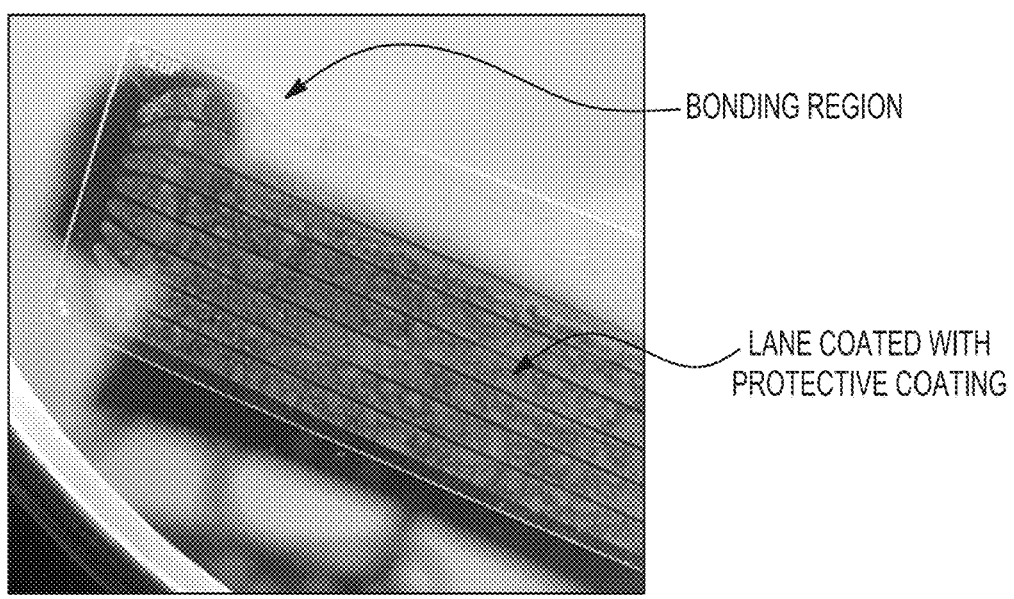
FIG. 11 is a black and white reproduction of an originally colored photograph of a portion of non-patterned glass slide having an example of a protective coating selectively applied to the lanes thereof via an example of the methods disclosed herein.

FIG. 11 illustrates a black and white reproduction of a photograph of a portion of the non-patterned glass slide after insoluble negative photoresist lift-off. As depicted, the protective coating was present in the lanes, and neither the insoluble negative photoresist nor the protective coating that had been deposited was present on the bonding regions.

Example 2

A method similar to that described in reference to FIG. 10 was used to apply PAZAM, pre-grafted with P5 and P7 primers, in the lanes of a patterned nanoimprint lithography resin over a glass wafer. The dimensions of the lanes were 4.5 mm wide and 120 mm long. The pre-grafted PAZAM was present in an aqueous solution at 0.3 wt %.

The precision gantry tool included a progressive cavity pump and a conical stainless steel nozzle with a 17 gauge tip. The air gap was set to about 65 μm and the flow rate was set to 2 μL/s.

The pre-grafted PAZAM was deposited into each lane of substrate, and was allowed to dry.

A hybridization-based CFR quality control test was performed. The CFR quality control test utilizes a CalFluor Red (a red dye) labeled oligonucleotide having complementary sequence to the P5/P7 primers. The CFR primers were introduced, hybridized to the P5/P7 primers on the surface, and the excess CFR primers were washed away. The attached dye concentration was measured by fluorescence detection.

FIG. 12 illustrates a grey scale fluorescence image of the patterned substrate after the quality control test. The dark lanes were indicative of high fluorescence intensity, and the white surrounding regions were indicative of low fluorescence intensity. These results demonstrated that the CFR primers hybridized to the pre-grafted PAZAM in the lanes. These results also demonstrated that no CFR primers hybridized to the bonding regions, as these regions lacked pre-grafted PAZAM for the primer hybridization.

Example 3

A method similar to that described in reference to FIG. 10 was used to apply KOLLICOAT® IR (a polyvinyl alcohol/polyethylene glycol graft copolymer available from BASF Corp.) in portions of the lanes of patterned nanoim print lithography resin on a glass wafer. The lanes were coated with PAZAM, which had fluorescently labeled oligonucleotides grafted thereto. The surrounding bonding regions did not have any PAZAM coated thereon. An aqueous solution was prepared with 15 wt % KOLLICOAT® IR. The aqueous solution was deposited into the lanes using the precision gantry tool with a progressive cavity pump and a conical stainless steel nozzle with a 17 gauge tip. The air gap was set to about 65 μm and the flow rate was set to 2 μL/s.

For comparison, the aqueous solution was deposited into the lanes using a comparative tool with a pressure based pump and a plastic conical nozzle with a 17 gauge tip. The air gap was at least 200 μm. The flow rate on the comparative tool cannot be controlled.

Figure 13C:
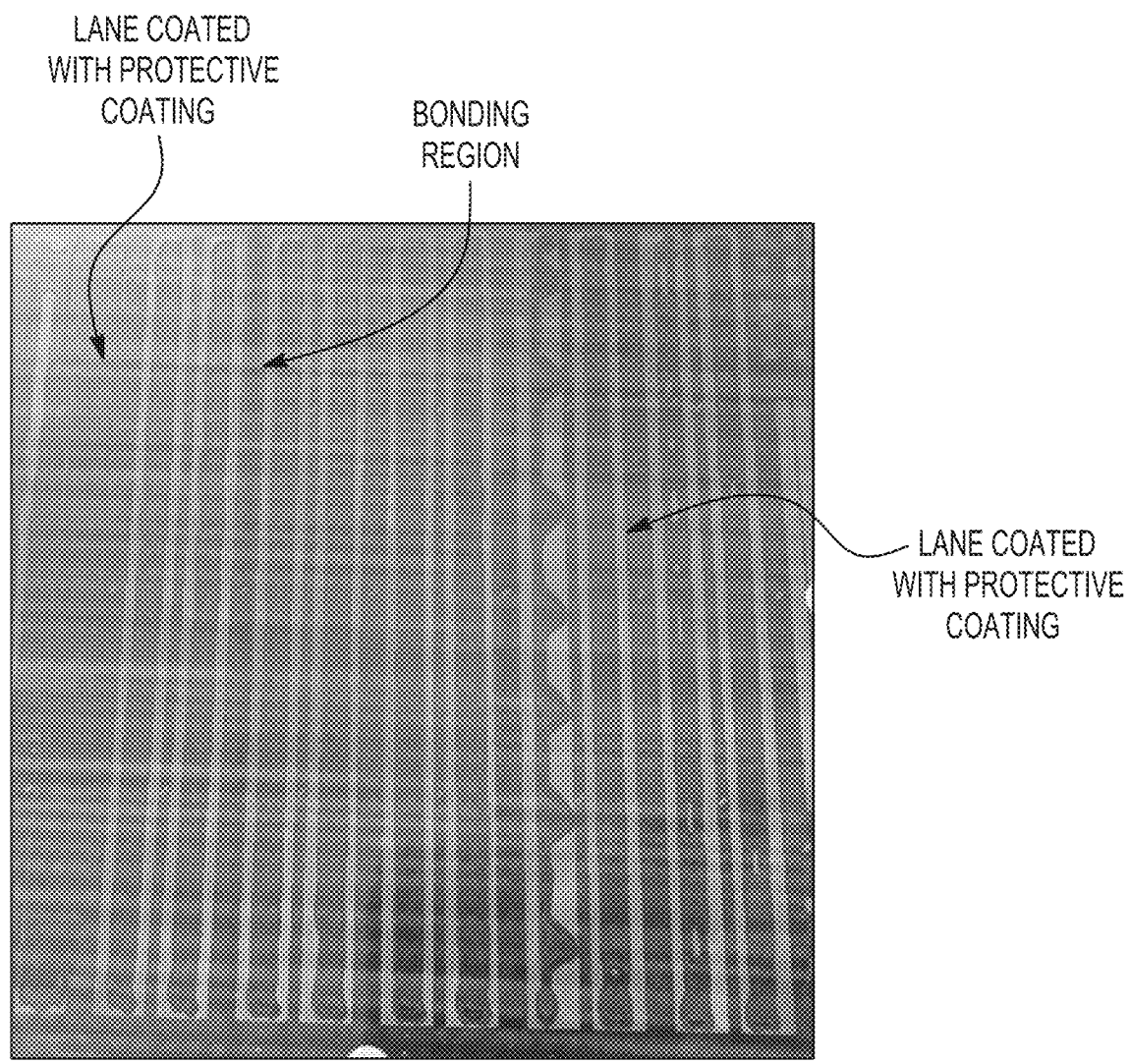

Fluorescence images of portions of some of the lanes and surrounding bonding regions were taken using a microscope after the aqueous solution was dispensed and dried. FIG. 13A depicts the example lanes and surrounding bonding regions and FIG. 13B and FIG. 13C depict the comparative example lanes and surrounding bonding regions at different magnifications. The center black portion in the lanes of FIG. 13A was the protective coating, which reduced the intensity of the underlying fluorophore. The surrounding white portion was the remainder of the lane that did not have the protective coating applied thereon. As shown in FIG. 13A, the line fidelity was precise for the example protective coatings. In contrast, the comparative protective coatings in FIG. 13B and FIG. 13C spread undesirably and thus the lines were not precise. This may have been due to the pressure based pump, which enables no control over the thickness or reflow of the applied materials.

For still another comparison, both screen printing and inkjet printing were attempted for depositing the aqueous solution. Screen printing failed due to mesh clogging and bubble generation in the applied coating. Inkjet printing failed due to clogged nozzles and jetting bubbles.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such values or sub-ranges were explicitly recited. For example, a range of about 400 nm to about 1 μm (1000 nm), should be interpreted to include not only the explicitly recited limits of about 400 nm to about 1 μm, but also to include individual values, such as about 708 nm, about 945.5 nm, etc., and sub-ranges, such as from about 425 nm to about 825 nm, from about 550 nm to about 940 nm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A method, comprising:
applying a water-soluble protective coating solution over a bonding region and over either i) a patterned region of a patterned structure, the patterned region including depressions having at least a polymeric hydrogel therein, and interstitial regions separating the depressions or ii) a lane region of a non-patterned structure, the lane region including a lane having at least the polymeric hydrogel therein;
drying the water-soluble protective coating solution to form a solid coating or a gel coating over the bonding region and over either i) the patterned region or ii) the lane region;
after drying the water-soluble protective coating solution:
applying a photoresist over the solid coating or the gel coating; and
patterning the photoresist to remove the photoresist from portions of the solid coating or the gel coating over the bonding region and to generate an insoluble photoresist over other portions of the solid coating or the gel coating over either i) the patterned region or ii) the lane region; and
selectively removing the portions of the solid coating or the gel coating from the bonding region while leaving the other portions of the solid coating or the gel coating over either i) the patterned region or ii) the lane region.

2. The method as defined in claim 1, wherein selectively removing the portions of the solid coating or the gel coating from the bonding region involves exposing the portions to a dry etch or a water rinse while the insoluble photoresist is in place.

3. The method as defined in claim 2, further comprising lifting off the insoluble photoresist in a remover, wherein the solid coating or the gel coating is insoluble in the remover.

4. A method, comprising:
- applying a water-soluble protective coating solution over a bonding region and over either i) a patterned region of a patterned structure, the patterned region including depressions having at least a polymeric hydrogel therein, and interstitial regions separating the depressions or ii) a lane region of a non-patterned structure, the lane region including a lane having at least the polymeric hydrogel therein, wherein:
  - the patterned structure or the non-patterned structure is a multi-layer stack including a transparent base support, a patterned mask layer over the transparent base support, and a patterned transparent layer over the patterned mask layer and the transparent base support; and
  - a pattern of the patterned mask layer corresponds with the bonding region;
- drying the water-soluble protective coating solution to form a solid coating or a gel coating over the patterned mask layer and the bonding region, and over either i) the patterned region or ii) the lane region;
- applying a negative photoresist over the solid coating or the gel coating;
- exposing the negative photoresist to light through the transparent base support, whereby portions of the negative photoresist overlying either i) the patterned region or ii) the lane region define the insoluble photoresist, and portions of the negative photoresist overlying the patterned mask layer and the bonding region become soluble; and
- selectively removing portions of the solid coating or the gel coating from the patterned mask layer the bonding region while leaving other portions of the solid coating or the gel coating over either i) the patterned region or ii) the lane region.

5. The method as defined in claim 4, wherein selectively removing the portions of the solid coating or the gel coating from the patterned mask layer and the bonding region involves exposing the portions to a developer of the negative photoresist.

6. The method as defined in claim 5, further comprising lifting off the insoluble photoresist in a solvent to which the solid coating or the gel coating is inert.

7. A method, comprising:
- applying a water-soluble protective coating solution over a bonding region and over either i) a patterned region of a patterned structure, the patterned region including depressions having at least a polymeric hydrogel therein, and interstitial regions separating the depressions or ii) a lane region of a non-patterned structure, the lane region including a lane having at least the polymeric hydrogel therein;
- drying the water-soluble protective coating solution to form a solid coating or a gel coating over the bonding region and over either i) the patterned region or ii) the lane region; selectively applying a metal layer over portions of the solid coating or the gel coating over either i) the patterned region or ii) the lane region;
- selectively removing other portions of the solid coating or the gel coating from the bonding region exposing the portions to a dry etch while the metal layer is in place; and
- after selectively removing the portions of the solid coating or the gel coating, removing the metal layer.

8. A method, comprising:
- applying a water-soluble protective coating solution over a bonding region and over either i) a patterned region of a patterned structure, the patterned region including depressions having at least a polymeric hydrogel therein, and interstitial regions separating the depressions or ii) a lane region of a non-patterned structure, the lane region including a lane having at least the polymeric hydrogel therein;
- drying the water-soluble protective coating solution to form a solid coating or a gel coating over the bonding region and over either i) the patterned region or ii) the lane region; and
- selectively removing portions of the solid coating or the gel coating from the bonding region while leaving other portions of the solid coating or the gel coating over either i) the patterned region or ii) the lane region by laser patterning the portions of the solid coating or the gel coating over the bonding region.

* * * * *